United States Patent [19]

Tanaka et al.

[11] Patent Number: 4,927,565
[45] Date of Patent: May 22, 1990

[54] 5-SUBSTITUTED AMINO-4-HYDROXY-PENTENOIC ACID DERIVATIVES AND THEIR USE

[75] Inventors: Seiichi Tanaka, Tokyo; Yutaka Koike, Koshigaya; Masato Nakano, Tokyo; Shugo Atsuumi, Tokyo; Hajime Morishima, Tokyo; Kenji Matsuyama, Kashiwa, all of Japan

[73] Assignee: Banyu Pharmaceutical Co., Ltd., Tokyo, Japan

[21] Appl. No.: 133,642

[22] Filed: Dec. 16, 1987

[30] Foreign Application Priority Data

Dec. 19, 1986 [JP] Japan .............................. 61-301596

[51] Int. Cl.$^5$ .......................... C09F 5/00; C09F 5/06
[52] U.S. Cl. ................................... 260/404.5; 514/17
[58] Field of Search ................. 260/404.5 PA; 514/17

[56] References Cited

U.S. PATENT DOCUMENTS

| | | | |
|---|---|---|---|
| 4,609,643 | 9/1986 | Szelke et al. | 514/17 |
| 4,713,367 | 12/1987 | Sisto et al. | 514/17 |
| 4,729,985 | 3/1988 | Kleinman et al. | 514/17 |
| 4,749,687 | 6/1988 | Bindra et al. | 514/17 |
| 4,757,050 | 7/1988 | Natarajnan et al. | 514/17 |

FOREIGN PATENT DOCUMENTS 0163237 12/1985 European Pat. Off. .

OTHER PUBLICATIONS

Hanson et al., *J. Org. Chem.*, vol. 50, pp. 5399–5401 (1985).
Search Report for European Patent Application 87 11 8570.8.

*Primary Examiner*—Patrick P. Garvin
*Assistant Examiner*—G. D. Irzinski
*Attorney, Agent, or Firm*—Oblon, Spivak, McClelland, Maier & Neustadt

[57] ABSTRACT

A 5-substituted amino-4-hydroxy-pentenoic acid or its salt represented by the formula:

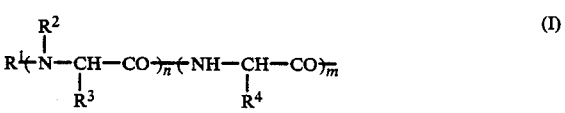

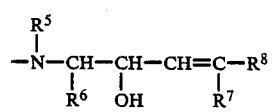

wherein each of $R^1$ and $R^2$ which may be the same or different is a hydrogen atom, a lower alkyl group, an aralkyl group, a lower alkoxycarbonyl group, an aryloxycarbonyl group, an aralkyloxycarbonyl group or a lower alkanoyl group which may be substituted by from one to three substituents selected from the group consisting of an amino group, a hydroxyl group, a carboxyl group, an aryloxy group, an aralkyloxycarbonylamino group, a lower alkoxycarbonylamino group and a

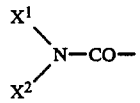

group (wherein each of $X^1$ and $X^2$ which may be the same or different is a hydrogen atom, a lower alkyl group, an aryl group or an aralkyl group, or $X^1$ and $X^2$ form together with the adjacent nitrogen atom a 5- or 6-membered heterocyclic group which may further contain a hetero atom selected from the group consisting of a nitrogen atom, an oxygen atom and a sulfur atom) and which may further contain a double bond in its carbon chain, each of $R^3$, $R^4$ and $R^6$ which may be the same or different is a hydrogen atom, a lower alkyl group, a cycloalkyl group, a cycloalkylalkyl group, an aryl group, an aralkyl group or a residue of an acidic neutral or basic amino acid, $R^5$ is a hydrogen atom or a lower alkyl group, $R^7$ is a hydrogen atom, a lower alkyl, cycloalkyl, cycloalkylalkyl or aralkyl group which may be substituted by one or two hydroxyl groups or a residue of an acidic, neutral or basic amino acid, $R^8$ is a hydroxymethyl group or a —CO—$R^9$ group (wherein $R^9$ is a hydroxyl group, a —OY group (wherein Y is a lower alkyl group, an aryl group, an aralkyl group, a lower alkoxyalkyl group, a lower alkanoyloxyalkyl group, a lower alkoxycarbonyloxyalkyl group, or a 1-phthalidyl group) or

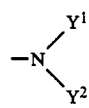

group (wherein each of $Y^1$ and $Y^2$ which may be the same or different is a hydrogen atom, a lower alkyl group, an aryl group, an aralkyl group or a cycloalkyl group, or $Y^1$ and $Y^2$ form together with the adjacent nitrogen atom a 5- or 6-membered heterocyclic group which may further contain a hetero atom selected from the group consisting of a nitrogen atom, an oxygen atom and a sulfur atom), and each of n and m which may be the same or different is 0 or 1.

11 Claims, No Drawings

5-SUBSTITUTED AMINO-4-HYDROXY-PENTENOIC ACID DERIVATIVES AND THEIR USE

The present invention relates to 5-substituted amino-4-hydroxy-pentenoic acids or their salts useful in the pharmaceutical field. More particularly, the present invention relates to 5-substituted amino-4-hydroxy-pentenoic acids or their salts which have renin inhibiting activities and which are thus expected to be useful as hypotensive drugs.

A renin-angiotensin system is one of the hypertensive systems in the living body, and it is an important system for regulating the blood pressure-body fluid electrolyte. Renin is secreted from renal juxtaglomerular cells and enters into the whole body circulation system via the renal vein. In the blood, there exists angiotensinogen which is a glycoprotein produced in the liver. Renin reacts on angiotensinogen to form angiotensin I. Most of angiotensin I will be converted to angiotensin II by angiotensin I-coverting enzyme which is present in the pulmonary vascular cells in one cycle of pulmonary circulation. Angiotensin II thus formed directly induces contraction of smooth muscles of peripheral blood vessels and thus shows a strong hypertensive activity. It further acts on the adrenal cortex to induce secretion of aldosterone, which in turn acts on the renal to facilitate reabsorption of sodium, whereby the effective circulatory blood flow increases, the heat rate increases and the peripheral vascular resistance increases so that the blood pressure increases.

It is known that hypertension will be brought about if this renin-angiotensin system progresses abnormally. Typical examples are renal vascular hypertension and malignant hypertension. Further, as a rare case, hypertension caused by a renin producing tumor is known.

For the treatment of the hypertension due to the progress of the renin-angiotensin system, inhibitors against the angiotensin I-converting enzyme have been studied, developed and subjected to clinical tests. However, such inhibitors are suspected to have side effects, since the substrate specificity of the angiotensin I-converting enzyme is broad to some extent and there exist some enzymes similar to the angiotensin I-converting enzyme in the living body. On the other hand, it is known that renin has a strict substrate specificity. Accordingly, an inhibitor against renin has a strong specificity and can be a superior hypotensive drug. For this reason, the research on renin inhibitors has been very active, and a number of renin inhibitors have been proposed, which may be classified into the following four categories.

1. Substrate Analogue Peptide

This has been attempted from the longest ago, and the change of amino acids in the renin substrate or the conversion of the L-amino acid to the D-amino acid has been proposed (Proc. Natl. Acad. Sci. USA, Vol. 77, p. 5476–5479 (1980), Biochem. Biophys. Res. Commun., Vol. 97, p. 230–235 (1980), Federation Proc., Vol. 42, p. 3155–3161 (1983), and Japanese Unexamined Patent Publication No. 10597/1986).

2. Statin or Statin Derivative-Containing Peptide

Statin is an uncommon amino acid contained in pepstatin which is a natural renin inhibitor produced by microorganisms (J. Antibiot., Vol. 23, p. 259–262 (1970), and Science, Vol. 175, p. 656 (1971)) and believed to play an important role for the development of the renin-inhibiting activity of pepstatin. A number of substrate analogue peptides of this statin have been synthesized (J. Med. Chem., Vol. 23, p. 27–33 (1980), Nature, Vol. 303, p. 81–84 (1983), J. Med. Chem., Vol. 28, p. 1553–1555 (1985), J. Cardiovasc. Pharmacol., Vol. 7 (Suppl. 4), p. s58–s61 (1985), J. Med. Chem., Vol. 28, p 1779–1790 (1985), Hypertension, Vol. 8, p. II-1 to II-5(1986), J. Med. Chem., Vol. 29, p. 2080–2087 (1986), J. Med. Chem., Vol. 29, p. 1152–1159 (1986), and Japanese Unexamined Patent Publications No. 89649/1984, No. 56194/1986, No. 186397/1986, No. 186398/1986, No. 29596/1987, No. 70349/1987, No. 163899/1985, No. 78795/1986, No. 152697/1986, No. 280459/1986, No. 275256/1986, No. 275257/1986, No. 275258/1986, No. 110661/1984, No. 252495/1985, No. 130257/ 1984, No. 90536/1983, No. 90539/1983, 105949/1983, No. 155345/1984, No. 34991/1985, No. 218398/1985, No. 218400/1985, No. 231695/1985, No. 243098/1985, No. 96/1986, No. 293957/1986, No. 100594/1986, No. 229851/1986 and No. 194097/1986).

3. Pseudo Peptide Having the Splitting Site of the Substrate Modified

A number of proposals have been made to modify the peptide bond at the site susceptible to hydrolysis in order to convert it to a bonding mode which is hardly susceptible to the hydrolysis and which is yet as close as the peptide bond.

(1) Hydroxyethylene type (Hypertension, Vol. 3, p. 13–18 (1985), Hypertension, Vol. 8, p. 1105–1112 (1986) and Japanese Unexamined Patent Publications No. 63641/1986, No. 136594/1985, No. 122296/1986, No. 53952/1987, No. 59846/1982, No. 500415/1985 and No. 293957/1986)

(2) Methylene amino type (carbonyl reduction type) (Nature Vol. 299, p. 555–557 (1982), Biochem. Biophys. Res. Commun., Vol. 139, p. 982–990 (1986), and Japanese Unexamined Patent Publications No. 500415/1985 and No. 59846/1982)

(3) Phosphinicomethylene type (Japanese Unexamined Patent Publications No. 33197/1987 and No. 26288/1987)

(4) Olefin type (J. Med. Chem., Vol. 27, p. 1351–1354 (1984))

(5) Retro-inverso amide type (Japanese Unexamined Patent Publications No. 231055/1984 and No. 231056/1984)

4. Others

Various inhibitors have been prepared by modifying those belonging to the above category 3.

(1) Aldehyde type (Biochem. Biophys. Res. Commun., Vol. 118, p. 929–933 (1984), Hypertension, Vol. 7 (Suppl. I), p. I-8 to I-11 (1985), FEBS Lett., Vol. 167, p. 273–276 (1984), Japanese Unexamined Patent Publications No. 100595/1986, No. 137896/1986, No. 148167/1986 and No. 227851/1984 and Japanese Examined Patent Publication No. 39149/1983)

(2) Glycol or thioglycol type (Biochem. Biophys. Res. Commun., Vol. 132, p. 155–161 (1985), Biochem. Biophys. Res. Commun., Vol. 143, p. 44–51 (1987), and Japanese Unexamined Patent Publications No. 33152/1986, No. 200970/1986, No. 33141/1987 and No. 263998/1986)

(3) Norstatin type (J. Med. Chem., Vol. 25, p. 605–610 (1982), Euro. J. Pharmacol., Vol. 129, p. 393–396 (1986) and Japanese Unexamined Patent Publications No. 176573/1986, No. 186366/1986, No. 236770/1986, No. 4286/1987, No. 33156/1987, No. 56458/1987 and No. 163899/1985)

(4) Hydroxyethyleneamino type (Biochem. Biophys. Res. Commun., Vol. 134, p. 71–77 (1986) and Japanese Unexamined Patent Publications No. 200970/1986, 118352/1986, No. 137897/1986, No. 136595/1985 and No. 33141/1987)

Among the above publications, Japanese Unexamined PCT Publication No. 500415/1985 and Japanese Unexamined Patent Publication No. 122296/1986 disclose compounds having a homostatin structure represented by the following formula:

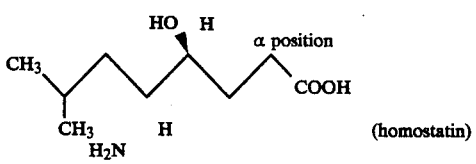

(homostatin)

Japanese Unexamined PCT Publication No. 500415/1985 discloses as a substituent at the α-position of homostatin a group of the formula —(CH$_2$)$_m$—NH$_2$ or —(CH$_2$)$_m$—OH wherein m is 2, 3 or 4. On the other hand, Japanese Unexamined Patent Publication No. 122296/1986 discloses as a substituent at the α-position of homostatin a lower alkyl group having at least two carbon atoms, a hydroxy-lower alkyl group which may be esterified or etherified, a cycloalkyl group, a cycloalkyl-lower alkyl group, a bicycloalkyl group, a bicycloalkyl-lower alkyl group, a tricycloalkyl group, a tricycloalkyl-lower alkyl group, an aryl group, an aryl-lower alkyl group, a carbamoyl group which may be substituted, a hydroxyl group which may be substituted or a mercapto group which may be substituted. However, both publications are based on the concept of the pseudo peptide having a splitting site of the substrate modified, and a substrate analogue amino acid side chain is sought as the substituent. Accordingly, there is no specific disclosure with respect to a lower alkyl group substituted by a hydroxyl group or a substituent substituted by a hydroxyl group. Likewise, there is no teaching or suggestion that excellent renin inhibiting activities can be obtained by the substitution with a hydroxyl group.

On the other hand, for the production of a statin derivative, it is known to obtain an optically highly pure statin derivative by the optical resolution of a mixture of diastereomers obtained by extending the carbon chain of a L-leucine as the starting material (Journal of Organic Chemistry, Vol. 43, p. 3624–3626 (1978), Japanese Unexamined Patent Publication No. 130257/1984 and Japanese Unexamined PCT Publication No. 500415/1985).

It is an object of the present invention to provide compounds which have excellent renin inhibiting activities and which are thus expected to be useful as hypotensive drugs.

The present inventors have paid attention to the statin moiety which plays an important role for the development of the renin inhibiting activity of pepstatin and have synthesized various statin derivatives and studied the renin inhibiting activities of such derivatives. As a result, it has been found that a group of compounds represented by the formula I given hereinafter exhibit excellent renin inhibiting activities. The present invention has been accomplished on the basis of this discovery.

The present invention provides a 5-substituted amino-4-hydroxy-pentenoic acid or its salt represented by the formula:

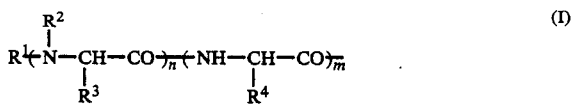

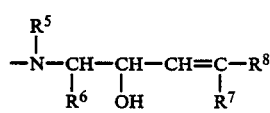

wherein each of R$^1$ and R$^2$ which may be the same or different is a hydrogen atom, a lower alkyl group, an aralkyl group, a lower alkoxycarbonyl group, an aryloxycarbonyl group, an aralkyloxycarbonyl group or a lower alkanoyl group which may be substituted by from one to three substituents selected from the group consisting of an amino group, a hydroxyl group, a carboxyl group, an aryloxy group, an aralkyloxycarbonylamino group, a lower alkoxycarbonylamino group and a

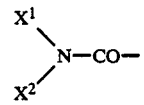

group (wherein each of X$^1$ and X$^2$ which may be the same or different is a hydrogen atom, a lower alkyl group, an aryl group or an aralkyl group, or X$^1$ and X$^2$ form together with the adjacent nitrogen atom a 5-or 6-membered heterocyclic group which may further contain a hetero atom selected from the group consisting of a nitrogen atom, an oxygen atom and a sulfur atom) and which may further contain a double bond in its carbon chain, each of R$^3$, R$^4$ and R$^6$ which may be the same or different is a hydrogen atom, a lower alkyl group, a cycloalkyl group, a cycloalkylalkyl group, an aryl group, an aralkyl group or a residue of an acidic, neutral or basic amino acid, R$^5$ is a hydrogen atom or a lower alkyl group, R$^7$ is a hydrogen atom, a lower alkyl, cycloalkyl, cycloalklalkyl or aralkyl group which may be substituted by one or two hydroxyl groups or a residue of an acidic, neutral or basic amino acid, R$^8$ is a hydroxymethyl group or a —CO—R$^9$ group (wherein R$^9$ is a hydroxyl group, a —OY group (wherein Y is a lower alkyl group, an aryl group, an aralkyl group, a lower alkoxyalkyl group, a lower alkanoyloxyalkyl group, a lower alkoxycarbonyloxyalkyl group, or a 1-phthalidyl group) or a

group (wherein each of Y$^1$ and Y$^2$ which may be the same or different is a hydrogen atom, a lower alkyl group, an aryl group, an aralkyl group or a cycloalkyl group, or Y$^1$ and Y$^2$ form together with the adjacent nitrogen atom a 5- or 6-membered heterocyclic group which may further contain a hetero atom selected from the group consisting of a nitrogen atom, an oxygen atom and a sulfur atom)), and each of n and m which may be the same or different is 0 or 1.

The present invention also provides a hypotensive drug which comprises an effective amount of the pentenoic acid or its salt of the formula I and a pharmaceutically acceptable carrier.

Further, the present invention also provides a process for producing the pentenoic acid or its salt of the formula I, which comprises reacting a compound of the formula:

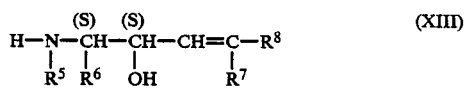

wherein $R^5$, $R^6$, $R^7$ and $R^8$ are as defined above, with a compound of the formula:

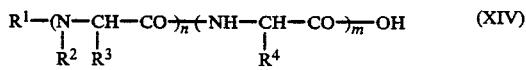

wherein $R^1$, $R^2$, $R^3$, $R^4$, n and m are as defined above.

Now, the present invention will be described in detail with reference to the preferred embodiments.

Firstly, the definitions of various terms referred to in this specification and some specific examples falling within such terms will be given.

The lower alkyl group may be a straight chain or branched alkyl group having from 1 to 6 carbon atoms such as a methyl group, an ethyl group, a propyl group, an isopropyl group, a butyl group, an isobutyl group, a sec-butyl group, a tert-butyl group, a pentyl group or a hexyl group.

The aryl group may be an aryl group having from 6 to 10 carbon atoms such as a phenyl group, a 3-methylphenyl group, a 4-methylphenyl group, a 4-ethylphenyl group, a 4-propylphenyl group, a 1-naphthyl group or a 2-naphthyl group.

The aralkyl group may be an aralkyl group having from 7 to 10 carbon atoms such as a benzyl group, a (1-naphthyl)methyl group, a (2-naphthyl)methyl group, a phenethyl group, a 3-phenylpropyl group or a 4-phenylbutyl group.

The cycloalkyl group may be a cycloalkyl group having from 3 to 6 carbon atoms such as a cyclopropyl group, a cyclobutyl group, a cyclopentyl group or a cyclohexyl group.

The cycloalkylalkyl group may be a cycloalkylalkyl group having from 4 to 8 carbon atoms such as a cyclopropylmethyl group, a cyclobutylmethyl group, a cyclopentylmethyl group, a cyclohexylmethyl group, a 1-cyclopropylethyl group, a 2-cyclopropylethyl group, a 1-cyclobutylethyl group, a 2-cyclobutylethyl group, a 1-cyclopentylethyl group, a 2-cyclopentylethyl group, a 1-cyclohexylethyl group or a 2-cyclohexylethyl group.

The lower alkoxycarbonylamino group may be a lower alkoxycarbonylamino group having from 2 to 7 carbon atoms such as a methoxycarbonylamino group, an ethoxycarbonylamino group, a propoxycarbonylamino group, an isopropoxycarbonylamino group, a butoxycarbonylamino group, an isobutoxycarbonylamino group, a tert-butoxycarbonylamino group, a pentyloxycarbonylamino group or a hexyloxycarbonylamino group.

The aryloxycarbonyl group may be an aryloxycarbonyl group having from 7 to 11 carbon atoms such as a phenoxycarbonyl group, a 4-methylphenyloxycarbonyl group, a 4-ethylphenyloxycarbonyl group, a 4-isopropylphenyloxycarbonyl group, a 4-tert-butylphenyloxycarbonyl group, a (1-naphthyl)oxycarbonyl group or a (2-naphthyl)oxycarbonyl group.

The aryloxy group may be an aryloxy group having from 6 to 10 carbon atoms such as a phenoxy group, a 4-methylphenyloxy group, a 4-ethylphenyloxy group, a 4-isopropylphenyloxy group, a (1-naphthyl)oxy group or a (2-naphthyl)oxy group.

The aralkyloxycarbonyl group may be an aralkyloxycarbonyl group having from 8 to 12 carbon atoms such as a benzyloxycarbonyl group, a phenethyloxycarbonyl group, a 3-phenylpropyloxycarbonyl group, a 4-phenylbutyloxycarbonyl group, a (1-naphthyl)methyloxycarbonyl group or a (2-naphthyl)methyloxycarbonyl group.

The aralkyloxycarbonylamino group may be an aralkyloxy carbonylamino group having from 7 to 12 carbon atoms such as a benzyloxycarbonylamino group, a phenethyloxycarbonylamino group, a 3-phenylpropyloxycarbonylamino group, a 4-phenylbutyloxycarbonylamino group, a (1-naphthyl)methyloxycarbonylamino group or a (2-naphthyl)methyloxycarbonylamino group.

The lower alkoxycarbonyl group may be a lower alkoxycarbonyl group having from 2 to 7 carbon atoms such as a methoxycarbonyl group, an ethoxycarbonyl group, a propoxycarbonyl group, an isopropoxycarbonyl group, a butoxycarbonyl group, a sec-butoxycarbonyl group, a tert-butoxycarbonyl group, a pentyloxycarbonyl group or a hexyloxycarbonyl group.

The lower alkoxyalkyl group may be a lower alkoxyalkyl group having from 2 to 7 carbon atoms such as a methoxymethyl group, an ethoxymethyl group, a 1-methoxyethyl group, 2-methoxyethyl group, a 1-ethoxyethyl group, a 2-ethoxyethyl group, a propoxymethyl group, an isopropoxymethyl group, a butoxymethyl group, an isobutoxymethyl group or a hexyloxymethyl group.

The lower alkanoyloxyalkyl group may be a lower alkanoyloxyalkyl group having from 3 to 7 carbon atoms such as an acetoxymethyl group, a propionyloxymethyl group, a butyryloxymethyl group, an isobutyryloxymethyl group, a valeryloxymethyl group, a pivaloyloxymethyl group, a 1-acetoxyethyl group, a 2-acetoxyethyl group, a 1-butyryloxymethyl group, a 2-butyryloxymethyl group, a 1-pivaloyloxyethyl group or a 2-pivaloyloxyethyl group.

The lower alkoxycarbonyloxyalkyl group may be a lower alkoxycarbonylalkyl group having from 3 to 9 carbon atoms such as a methoxycarbonyloxymethyl group, an ethoxycarbonyloxymethyl group, a propoxycarbonyloxymethyl group, an isopropoxycarbonyloxymethyl group, a butoxycarbonyloxymethyl group, a tert-butoxycarbonyloxymethyl group, a 1-methoxycarbonyloxyethyl group, 2-methoxycarbonyloxyethyl group, a 1-ethoxycarbonyloxyethyl group, a 2-ethoxycarbonyloxyethyl group, a 1-tert-butoxycarbonyloxyethyl group, a 2-tert-butoxycarbonyloxyethyl group, a 1-butoxycarbonyloxyethyl group, a 1-pentyloxycarbonyloxyethyl group or a 1-hexyloxycarbonyloxyethyl group.

In the

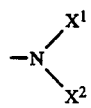

group wherein $X^1$ and $X^2$ are as defined above and the

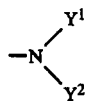

group wherein $Y^1$ and $Y^2$ are as defined above, when $X^1$ and $X^2$ or $Y^1$ and $Y^2$ form together with the adjacent nitrogen atom a 5- or 6-membered heterocyclic group which may further contain a hetero atom selected from the group consisting of a nitrogen atom, an oxygen atom and a sulfur atom, such as 5- or 6-membered heterocyclic group may be a morpholino group, thiomorpholino group, a pyrrolidinyl group or a piperazinyl group.

The residue of an acidic, neutral or basic amino acid may be a residue of an amino acid such as alanine, arginine, histidine, homoserine, leucine, naphthylalanine, norleucine, lysine, norvaline, ornithine, serine, threonine, tyrosine, valine, aspartic acid, glutamic acid, tryptohan, isoleucine, phenylalanine or cysteine.

The lower alkanoyl group which may be substituted by one to three substituents selected from the group consisting of an amino group, a hydroxyl group, a carboxyl group, an aryloxy group, an aralkyloxycarbonylamino group, a lower alkoxycarbonylamino group or a

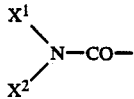

group wherein $X^1$ and $X^2$ are as defined above and which may further contain a double bond in the carbon chain, may be a lower alkanoyl group which may be substituted, such as an acetyl group, a propionyl group, a butyryl group, an isobutyryl group, a valeryl group, an isovaleryl group, an hexanoyl group, a phenoxyacetyl group, a (1-naphthyl)oxyacetyl group, a cinnamoyl group, a (2-naphthyl)oxyacetyl group, a 3-phenylpropanoyl group, a 3-phenyl-2-hydroxypropanoyl group, a 3-phenyl-2-phenylpropanoyl group, a 3-phenyl-2-benzylpropanoyl group, a 4-phenyl-2-benzylbutyryl group, a 5-phenyl-2-benzylpentanoyl group, a 2-benzyl-4-phenyl-3-butenoyl group, a 4-benzyloxycarbonylaminobutyryl group, a 3-methoxycarbonyl-2,3-dihydroxypropionyl group, a 3-morpholinocarbonyl-2-[(1-naphthyl)methyl]-propanoyl group, a 3-morpholinocarbonyl-2-[(2-naphthyl)methyl]-propanoyl group or a 4-aminobutyryl group.

The lower alkyl, cycloalkylalkyl or aralkyl group which is substituted by one or two hydroxyl groups includes a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a cyclohexylmethyl group, a cyclobutylmethyl group, a cyclopentylmethyl group, a cyclopropylmethyl group, a benzyl group, a phenetyl group, a 3-phenylpropyl group, a 1-phenylethyl group, a 3-cyclohexylpropyl group, a 2-cyclohexylethyl group, a 2-cyclopentylethyl group, a hydroxymethyl group, a 2-hydroxyethyl group, a 3-hydroxypropyl group, a 4-hydroxybutyl group, a 5-hydroxypentyl group, a 2,3-dihydroxypropyl group, a 3,4-dihydroxybutyl group, a 4,5-dihydroxypentyl group, a 1-hydroxyethyl group, a 1-hydroxypropyl group, a 1-hydroxybutyl group, a 1-hydroxypentyl group, a 2-hydroxy-1-hydroxymethylethyl group, a 3-hydroxy-2-hydroxymethylpropyl group, a 4-hydroxy-3-hydroxymethylbutyl group, a 3-hydroxy-2,2-dihydroxymethylpropyl group, a 4-hydroxy-2,3-dihydroxymethylbutyl group, a 2-hydroxymethyl-2,3-dihydroxypropyl group, a 2-hydroxymethylbutyl group, a 4-hydroxymethylbutyl group, a 3-hydroxy-3-cyclohexylpropyl group, a 4-hydroxy-4-cyclohexylbutyl group, a 3-hydroxy-3-cyclopentylpropyl group, a 4-hydroxy-4-cyclopentylbutyl group, a 4-hydroxybenzyl group, a 3-hydroxybenzyl group, a 2-hydroxybenzyl group, a 4-hydroxypgenethyl group, a 3-hydroxyphenethyl group, a 2-hydroxyphenethyl group, an α-hydroxybenzyl group, a 2-phenyl-2-hydroxyethyl group, a 2-phenyl-1-hydroxyethyl group and a 3-phenyl-3-hydroxypropyl group.

In the compound of the formula I of the present invention, the asymmetric carbon atoms may have R-configuration, S-configuration or RS-configuration.

When the compound of the present invention is in the form of a salt, such a salt may be any pharmaceutically acceptable non-toxic salt. For example, it may be a salt with an inorganic acid such as hydrochloric acid, sulfuric acid, hydrobromic acid or phosphoric acid, or a salt with an organic acid such as oxalic acid, maleic acid, acetic acid, formic acid or tartaric acid.

Now, the process for the preparation of the compound of the present invention will be described.

The compound of the formula I of the present invention can be produced by a process which will be described below.

A corresponding L-amino acid may usually be employed as the starting material. Firstly, the amino group of the amino acid is protected by a usual amino-protecting group e.g. an alkyloxycarbonyl group such as a benzyloxycarbonyl group, a p-methoxybenzyloxycarbonyl group or a tert-butyloxycarbonyl group, an aralkyloxycarbonyl group, a diacyl group such as a phthaloyl group, an acyl group such as a trifluoroacetyl group or a dichloroacetyl group, or an aralkyl group such as a benzyl group or a trityl group, then the carboxylic acid is preferably converted to an amide, an ester, an acid halide or an acid anhydride, and then the material is reduced by a conventional method such as Birch reduction, catalytic reduction or reduction by means of a metal hydride complex compound to form an aldehyde having the formula:

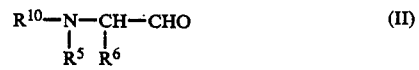 (II)

wherein $R^{10}$ is an amino-protecting group, and $R^5$ and $R^6$ are as defined above. A suitable method is selected depending upon the type of the amino group or the protecting group on the amino acid side chain. For instance, in the case of L-benzyloxycarbonylleucine, it is converted to pyrazolide by means of a condensing agent such as pyrazole and dicyclohexylcarbodiimide followed by the reduction with a metal hydride compound such as lithium aluminum hydride to obtain L-benzyloxycarbonylleucinal.

The aldehyde of the formula II is treated with a cyanide such as sodium cyanide or potassium cyanide, if necessary after converting it into an adduct with acid sodium sulfite, to obtain cyanohydrin, and then the nitrile group is hydrolyzed with an acid or base to obtain a compound having the formula:

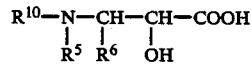
(III)

wherein $R^5$, $R^6$ and $R^{10}$ are as defined above. The compound of the formula III is obtainable in the form of a mixture of diasteroisomers, which may be separated by a usual separating means such as column chromatography or a high speed liquid chromatography. One of such specific methods for the synthesis is described in detail in Agricultural Biological Chemistry, Vol. 46, p. 1865–1872 (1982).

For instance, when a compound of the formula III having a R-configuration at the α-position is employed, the hydroxyl group of the compound III may be protected, if necessary, by a usual hydroxyl-protecting group such as a 2-methoxyethoxymethyl group, a 2-methoxyethyl group, a methoxymethyl group, a tetrahydropyranyl group, a 2-methoxytetrahydrofuranyl group, a 2-methoxytetrahydropyranyl group, a trimethylsilyl group, a tert-butyldimethylsilyl group, an acetyl group, a chloroacetyl group, a benzoyl group, a benzyl group or a p-methoxybenzyl group. In accordance with the above-mentioned method wherein the L-amino acid is converted to the compound of the formula II, the carboxylic acid is converted to a carboxylic acid amide, a carboxylic acid ester, an acid halide or an acid anhydride, then, the compound is reduced by a conventional method such as Birch reduction, catalytic reduction or a reduction by means of a metal hydride complex compound, whereby it is possible to obtain a compound having the formula:

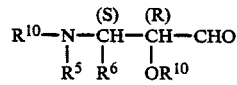
(IV)

wherein $R^{11}$ is a hydrogen atom or a hydroxyl-protecting group, and $R^5$, $R^6$ and $R^{10}$ are as defined above.

Further, a compound of the formula IV can be stereospecifically produced from statin, as the starting material, having the formula:

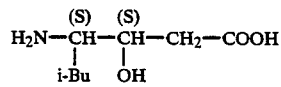
(V)

wherein i-Bu is an isobutyl group, which is obtained by hydrolyzing pepstatin known as aspartylprotease inhibitor, as disclosed in Japanese Patent Application No. 173,564/1986.

Namely, the amino group and the hydroxyl group in statin of the formula V may be protected, if necessary, by protecting groups suitable for the respective functional groups. Then, the carboxylic acid is reduced to an alcohol. In same cases, it is preferred to convert the carboxylic group to an lower alkyl ester before the reduction. The convertion is conducted by a conventional esterification method which does not adversely affect other substituents, for example by reacting it with a lower alkanol such as methanol or ethanol in the presence of an acid catalyst such as hydrochloric acid, hydrobromic acid or p-toluenesulfonic acid, or reacting it with diazomethane in the case of methyl esterification, whereby a compound having the formula:

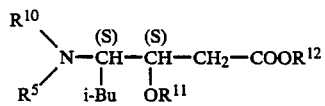
(VI)

wherein $R^5$, $R^{10}$, $R^{11}$ and i-Bu are as defined above, and $R^{12}$ is a lower alkyl group is obtained. In this step, the order of introducing substituents to the functional groups may be changed as the case requires.

The compound of the formula VI can be converted to a compound having the formula:

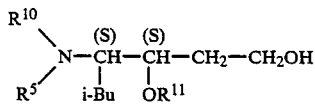
(VII)

wherein $R^5$, $R^{10}$, $R^{11}$ and i-Bu are as defined above, by a conventional method for reducing the carboxylate group to an alcohol, for instance, by reducing it with a metal hydride complex compound such as sodium borohydride or lithium borohydride in a solvent such as methanol, ethanol or tetrahydrofuran.

The hydroxyl group newly formed in the compound of the formula VII is reacted with p-toluenesulfonylchloride, methanesulfonylchloride or acetylchloride in the presence of a base such as pyridine or triethylamine to introduce a leaving group such as a methanesulfonyl group or an acetyl group, and then reacted with halogen donating agent such as lithium chloride or lithium bromide, whereby a compound having the formula:

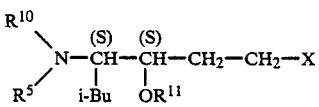
(VIII)

wherein $R^5$, $R^{10}$, $R^{11}$ and i-Bu are as defined above and X is a halogen atom, is obtained.

The compound of the formula VIII is converted to a compound having the formula:

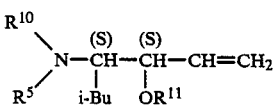
(IX)

wherein $R^5$, $R^{10}$, $R^{11}$ and i-Bu are as defined above, by treating it with an organic amine such as triethylamine or 1,8-diazabicyclo[5,4,0]-7-undecene, an alkali metal or alkaline earth metal hydroxide such as sodium hydroxide, potassium hydroxide or barium hydroxide, or an alkali metal alcoholate such as sodium methoxide, potassium methoxide or potassium tert-butoxide.

The compound of the formular IX is treated with an oxidizing agent such as chromic acid, a periodate, osmium tetraoxide, ozone or a combination of these agents, whereby the compound having the formula IV wherein $R^6$ is an isobutyl group, is produced stereospecifically.

The compound of the formula IV is reacted with a compound having the formula:

wherein Y is an oxygen atom or a sulfur atom, Z is nil, an oxygen atom or a nitrogen atom, $R^{13}$ is a lower alkyl group or an aryl group, and $R^7$ and $R^8$ are as defined above, or the formula:

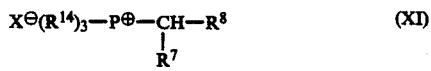

wherein X is a halogen atom, $R^{14}$ is an aryl group, and $R^7$ and $R^8$ are as defined above, preferably in a stream of an inert gas such as argon or nitrogen, in a solvent not adversely affecting the reaction, such as tetrahydrofuran or dimethylformamide, if necessary by an addition of a halide of an alkali metal or an alkaline earth metal, such as lithium chloride, lithium bromide or magnesium bromide, and further by an addition of a base e.g. a tertiary amine such as diazabicycloundecene, triethylamine or diisopropylethylamine, or a hydride, hydroxide, alcoholate or alkylated product of an alkali metal such as sodium hydride, sodium hydroxide, sodium ethoxide or butyl lithium, to obtain a compound having the formula:

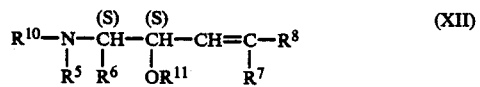

wherein $R^5$, $R^6$, $R^7$, $R^8$, $R^{10}$ and $R^{11}$ are as defined above. When $R^5$ is a lower alkyl group, the preferred stage for its introduction differs depending upon the particular alkylation method. For example, although the production according to this process may be carried out by using an N-alkylamino acid as the starting material, it is preferred to introduce a lower alkyl group, for instance, by reacting an alkyl halide such as methyliodide or ethyliodide to the compound of the formula XII in the presence of a base such as triethylamine.

Then, the protecting groups $R^{10}$ and $R^{11}$ are removed by a conventional method suitable for the removal of such protecting groups to obtain a compound having the formula:

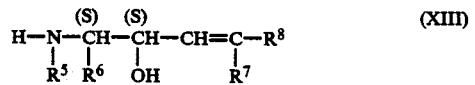

wherein $R^5$, $R^6$, $R^7$ and $R^8$ are as defined above.

The compound of the formula XIII is reacted with a compound having the formula:

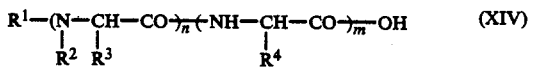

wherein $R^1$, $R^2$, $R^3$, $R^4$, n and m are as defined above, by a usual method for the peptide synthesis, such as an azide method, an activated ester method, a mixed acid anhydride method, a carbodiimide method, an imidazole method, a diphenylphosphorylazide method, a Woodward method or a condensation method in an oxidation-reduction system, to obtain a compound of the formula I of the present invention.

The order for linking such constituting components may not necessarily follow the above sequence and may suitably be selected depending upon the particular compound to be produced.

When the compound of the present invention is to be used as a medicine, it may be administered by itself, but it is usually administered as a mixture with a carrier suitably selected depending upon the route for administration and standard formulations. For example, for oral administration, the compound of the present invention may be administered in the form of tablets which may be prepared by adding to a powder of the active ingredient of the present invention an excipient such as starch, lactose, sucrose, glucose, crystalline cellulose, calcium carbonate or kaolin, a binder such as starch solution, a gelatin solution, a hydroxypropyl cellulose, a glucose solution, a sucrose solution, water or ethanol, a disintegrator such as starch, agar, gelatin powder, CMC-Ca, CMC-Na, crystalline cellulose, calcium carbonate or sodium hydrogencarbonate, or a lubricant such as magnesium stearate, calcium stearate, talc, macrogoal 4,000, marcogoal 6,000 or stearic acid, subjecting the mixture to compression molding by a conventional tabletting method, and if necessary, applying a sugar coating by means of a concentrated sugar solution containing e.g. gum arabic, talc, polyvinyl pyrrolidone, polyethylene glycol and/or titanium oxide, applying a film coating by means of a film-forming agent composed of e.g. polyvinyl acetal, diethylaminoacetate, cellulose acetate, N,N-dibutylaminohydroxypropyl ether, hydroxypropylmethyl cellulose, hydroxypropyl cellulose, ethyl cellulose or polyvinyl pyrrolidone, or applying an enteric coating by means of a film-forming agent composed of e.g. ethyl cellulose phthalate cerac, cellulose acetate phthalate or hydroxypropylmethyl cellulose phthalate; granules or fine granules which may be prepared by adding to the active ingredient of the present invention a binder such as starch, gelatin, gum arabic, methyl cellulose, sodium carboxymethyl cellulose, heavy silicic anhydride or light silicic anhydride, followed by kneading and granulation by usual methods; a powder of the active ingredient of the present invention by itself; or capsules which may be prepared by adding to the active ingredient of the present invention an excipient such as lactose, starch or crystalline cellulose and/or a lubricant such as magnesium stearate, calcium stearate or talc, and filling the mixture into capsules. For non-oral administration, an injection formulation may be used wherein an emulsifying agent such as propylene glycol, polyethylene glycol or a vegetable oil such as olive oil, or a solubilization agent such as sodium benzoate, sodium salicyate, N-hydroxyethyllactamide, calcium α-saccharide, mannitol, nicotic acid amide or cyclodextrin, is suitably used.

Further, to such formulations, other medicinal substances may be incorporated. Such medicinal substances include, for example, acetazolamide, amiloride, chlorothiazide, furosemide, timolol, propranolol, cetamolol, clonidine, methyldopa, minoxydil, hydralazine, captopril, pivalopril, enalapril, lidinopril, verapamil, nifedipine, nicardipine, felodipine, nimodipine and diltiazem.

An advantageous formulation contains from about 0.1 mg to 500 mg of the compound of the present invention. A preferred range of a daily dose for oral administration is from about 0.1 mg/kg to 500 mg/kg, and such a daily dose may be administered at once or in three times a day. For non-oral administration, it is preferred to administer the compound of the present invention in an amount of from about 0.1 mg/kg to 10 mg/kg per day at once. The dose may be increased or reduced by a doctor's prescription depending upon e.g. the sex and diseased condition of the patient.

Now, the present invention will be described in further detail with reference to the Test Example for renin inhibiting activities of the compounds of the present invention and Working Examples.

TEST EXAMPLE FOR RENIN INHIBITING ACTIVITIES

To 156 μl of a 0.2M sodium phosphate buffer solution (pH7.4), 40 μl of a solution mixture of 43 mM 8-hydroxyquinoline and 100 mM disodium ethylenediamine tetraacetate, 4 μl of dimethyl sulfoxide or a dimethyl sulfoxide solution of an inhibitor and 200 μl of human plasma were added and reacted at 37° C. for one hour. Then, pepstatin was added thereto to terminate the reaction, and the amount of the resulting angiotension I was measured by radio immunoassay whereby the inhibiting activity was determined. The 50% inhibition concentrations ($IC_{50}$ values) of the compounds of the present invention are shown below.

TABLE 1
Human plasma renin inhibiting activities

| Compound | 50% inhibition concentration $IC_{50}$ (mol) |
|---|---|
| A | $1.4 \times 10^{-6}$ |
| B | $1.9 \times 10^{-8}$ |
| C | $6.7 \times 10^{-8}$ |
| D | $1.2 \times 10^{-7}$ |
| E | $3.1 \times 10^{-7}$ |
| F | $1.5 \times 10^{-7}$ |
| G | $2.6 \times 10^{-7}$ |
| H | $1.6 \times 10^{-7}$ |

Compound A: Compound of Example 1
Compound B: Compound of Example (2-3)
Compound C: Compound of Example (2-4)
Compound D: Compound of Example (3-3)
Compound E: Compound of Example (3-4)
Compound F: Compound of Example (4-3)
Compound G: Compound of Example (4-4)
Compound H: Compound of Example 6

Now, the present invention will be described with reference to Examples. However, it should be understood that the present invention is by no means restricted by these specific Examples.

EXAMPLE 1

(4S,5S)-5-(L-N-benzyloxycarbonylnaphthylalanyl-L-norleucyl)amino-4-hydroxy-7-methyl-2(E)-octenoic acid isobutylamide (1) 247 mg of lithium chloride was suspended in 25 ml of dry tetrahydrofuran under an argon gas stream, and 1.0 ml of ethyl-α-diethylphosphono acetate was dropwise added thereto under stirring. The mixture was stirred for 5 minutes at room temperature, and then a solution prepared by dissolving 1.43 g of (4S,5R)-3-benzyloxycarbonyl-2,2-dimethyl-5-formyl-4-isobutyloxazolidine in 2.0 ml of dry tetrahydrofuran, was added thereto. The mixture was stirred overnight at room temperature. After the completion of the reaction, the precipitated inorganic salt was filtered off, and the reaction solution was neutralized with 1N hydrochloric acid under cooling with ice. The reaction solution was concentrated under reduced pressure. A syrup thereby obtained was dissolved in 150 ml of benzene and washed with 100 ml of water. The separated aqueous layer was further extracted with 75 ml of benzene. The organic layers were put together, dried over anhydrous magnesium sulfate and concentrated under reduced pressure. A syrup thereby obtained was purified by silica gel column chromatography (27 g of Kieselgel 60) by using a mixture of benzene/ethyl acetate (30/1) to obtain 1.10 g of ethyl 3-[(4S,5S)-3-benzyloxycarbonyl-2,2-dimethyl-4-isobutyloxazolidin-5-yl]-2(E)-propenoate as a colorless syrup.

$R_f$: 0.51(silica gel plate, developer:

--- n-hexane/ethyl acetate (3/1))
Mass spectrum (FAB-MS) m/z $390(M^+ + 1)$
$374(M^+ - .CH_3)$ $346(M^+ - .CH-CH_3)$
            $|$
            $CH_3$ NMR(60MHz, CDCl$_3$)

δ ppm: 0.7–1.1(6H,m), 1.1–1.9[12H, 1.3 ppm (3H, t, J = 6.5Hz), 1.5 and 1.6 ppm (3H × 2, s × 2)], 3.9(1H, m), 4.2(2H, q, J = 7Hz), 4.5(1H, ddd, Ja = 1.5Hz, Jb = 3Hz, Jc = 6Hz), 5.1(2H, s), 6.05(1H, dd, Jd = 15 Hz, Ja = 1.5Hz), 7.0(1H, dd, Jc = 6Hz, Jd = 15Hz), 7.35(5H, s)
$[\alpha]_D^{20} - 34.1°$ (C = 1.14, chloroform)

---

(2) 930 mg of ethyl 3-[(4S,5S)-3-benzyloxycarbonyl-2,2-dimethyl-4-isobutyloxazolidin-5-yl]-2(E)-propenoate was dissolved in 1 ml of ethanol, and 10 ml of ethanol containing 790 mg of potassium hydroxide was added thereto at 0° C. The mixture was stirred for 1 hour at room temperature, then adjusted to pH2 with 1N hydrochloric acid and extracted with ethyl acetate. The organic layer was washed sequentially with water and a saturated sodium chloride aqueous solution and then dried over anhydrous magnesium sulfate. Then, the solvent was distilled off under reduced pressure to obtain 3-[(4S,5S)-3-benzyloxycarbonyl-2,2-dimethyl-4-isobutyloxazolidin-5-yl]-2-(E)-propenoic acid as a colorless oily substance.

Without purification, this propenoic acid was dissolved in 5 ml of dry dimethylformamide, and 3 ml of dry dimethylformamide containing 290 mg of triethylamine and 790 mg of diphenylphosphorylazide, and 3 ml of dry dimethylformamide containing 228 mg of isobutylamine were sequentially dropwise added thereto at −20° C. under stirring. After stirring for 1 hour at −10° C. and further stirring overnight at room temperature, the solvent was distilled off under reduced pressure. The residue was dissolved in 50 ml of ethyl acetate, washed sequentially with a 4% sodium hydrogen carbonate aqueous solution, water and saturated sodium chloride aqueous solution and dried over anhydrous magnesium sulfate. The solvent was distilled off under reduced pressure and the residue was purified by silica gel column chromatography (80 g of Kieselgel 60) by using a mixture of n-hexane/ethyl acetate (5/1) and further purified by thin-layer chromatography (Kieselgel 60) by using a mixture of n-hexane/ethyl acetate (⅔) to obtain 570 mg of 3-[(4S,5S)-3-benzyloxycarbonyl-2,2-dimethyl-4-isobutyloxazolidin-5-yl]-2(E)-propenoic acid isobutylamide as a colorless crystal.

$R_f$: 0.61 (silica gel plate,
developer: n-hexane/ethyl acetate (1/1))
NMR(60 MHz, CDCl$_3$): δppm: 0.7–1.2(12H, m), 1.2–2.2[10H, 1.52(3H, s), 1.61(3H, s)], 3.12 (2H, dd, Ja=6 Hz, Jb=6 Hz), 3.7–4.1(1H, m), 4.3–4.6(1H, m), 5.10(2H, s), 5.95(1H, d, Jc=15 Hz), 6.80(1H, dd, Jc=15 Hz, Jd=6 Hz), 7.28(5H, s).

(3) 555 mg of 3-[(4S,5S)-3-benzyloxycarbonyl-2,2-dimethyl-4-isobutyloxazolidin-5-yl]-2(E)-propenoic acid isobutylamide was dissolved in 10 ml of acetonitrile and 1.8 g of sodium iodide and 1.16 g of trimethylsilyl chloride were added thereto. The mixture was stirred for 1.5 hours under heating at 45° C. under a nitrogen atmosphere and a 10% hydrogen chloride-methanol solution was added to the reaction solution. The mixture was stirred for 15 minutes at room temperature and the solvent was distilled off under reduced pressure. The residue was dissolved in 20 ml of water and extracted with diethyl ether. The ether layer was extracted with a 0.5N hydrochloric acid and the extract was adjusted to about pH 10 with sodium carbonate. Sodium chloride was added thereto until it was saturated, and the product was extracted with ethyl acetate. The ethyl acetate layer was dried over anhydrous magnesium sulfate and the solvent was distilled off under reduced pressure to obtain 200 mg of (4S,5S)-5-amino-4-hydroxy-7-methyl-2(E)-octenoic acid isobutylamide as a colorless powder.

$R_f$: 0.35 (silica gel plate, developer:
chloroform/methanol/33% acetic acid, (6/2/0.5))
NMR(60 MHz, CD$_3$OD): δppm: 6.08(1H, d, Ja=16 Hz), 6.65(1H, dd, Ja=16 Hz, Jb=8 Hz).

(4) 217 mg of L-N-benzyloxycarbonylnaphthylalanyl-L-norleucinehydrazide was dissolved in 1 ml of dimethylformamide and 0.34 ml of a 4N hydrogen chloride/dioxane was added thereto. The mixture was cooled to −60° C. and 0.99 ml of isoamyl nitrite was added thereto. The temperature of the mixture was raised to −20° C. After confirming that the hydrazide disappeared, the temperature of the mixture was lowered to −60° C. The mixture was neutralized by adding 0.15 ml of N-methylmorpholine and then 1.5 ml of a dimethylformamide solution containing 100 mg of (4S,5S)-5-amino-4-hydroxy-7-methyl-2(E)-octenoic acid isobutylamide was added thereto. The mixture was stirred overnight at 8° C. and precipitates were filtered off. The solvent was distilled off under reduced pressure and ethyl acetate was added to the residue. The precipitated crystal was collected by filtration to obtain 43 mg of (4S,5S)-5-(L-N-benzyloxycarbonylnaphthylalanyl-L-norleucyl)amino-4-hydroxy-7-methyl-2(E)-octenoic acid isobutylamide (Compound A) as a colorless powder.

$R_f$: 0.33(silica gel plate, developer:
chloroform/methanol (15/1))
Melting point: 250.5°–252° C.
Mass spectrum: m/z 687(M$^+$+1)
NMR(60 MHz, DMSO-d$_6$): δppm: 4.88(2H, s), 6.05(1H, d, Ja=15 Hz), 6.62(1H, dd, Ja=15 Hz, Jb=4 Hz), 7.0–8.5(12H, m).

EXAMPLE 2

(4S,5S)-5-(L-N-benzyloxycarbonylnaphthylalanyl-L-norleucyl)amino-2-ethyl-4-hydroxy-7-methyl-2-octenoic acid isobutylamide (1) Ethyl 2-diethylphosphonobutanoate 856 mg of a sodium hydride dispersion (60% in oil) was washed three times with n-hexane under a nitrogen atmosphere to separate the oil. After drying, the powder obtained was suspended in 7.2 ml of dry dimethylformamide under a nitrogen atmosphere, and 4.26 ml of ethyl diethylphosphono acetate was dropwise added under stirring over a period of 1 hour at 0° C. The mixture was stirred at room temperature for about 1 hour and then cooled to 0° C. Then, 1.92 ml of bromoethane was added thereto under stirring and the mixture was stirred overnight at 55° C.

The reaction mixture was poured into 40 ml of water and extracted three times with 20 ml of ethyl acetate. The organic layer was washed sequentially with water and a saturated sodium chloride aqueous solution and then dried over anhydrous sodium sulfate. Then, the solvent was distilled off under reduced pressure, and the residue was purified by silica gel column chromatography (120 g of kiesel gel 60) by using a mixture of n-hexane/acetone (4/1) to obtain 2.76 g of the above-identified compound as an oily substance.

$R_f$: 0.63 (silica gel plate, developer:
n-hexane/ethyl acetate (1/5))
Mass spectrum m/z 253(M$^+$+1)
NMR(60 MHz, CDCl$_3$): δppm: 0.95(3H, t, J=8 Hz), 1.25(3H, t J=8 Hz), 1.29(6H, t, J=7 Hz), 1.6–2.1(2H, m), 2.8(1H, ddd, J=22, 7, 7 Hz), 4.05(2H, q, J=8 Hz), 4.15(2H, q, J=7 Hz).

(2) 3-[(4S,5S)-3-benzyloxycarbonyl-2,2-dimethyl-4-isobutyloxazolidin-5-yl]-2-ethyl-2-propenoic acid isobutylamide (a) 71.6 mg of lithium chloride was suspended in 5 ml of dry tetrahydrofuran in an argon atmosphere, and a solution prepared by dissolving 426 mg of ethyl 2-diethylphosphonobutanoate in 0.6 ml of dry tetrahydrofuran, was added thereto under stirring. The mixture was stirred for 5 minutes at room temperature, and then a 50% dry tetrahydrofuran solution containing 323 mg of diazabicycloundecene was added thereto. The mixture was stirred for 10 minutes at room temperature. Then, a solution prepared by dissolving 450 mg of (4S,5R)-3-benzyloxycarbonyl-2,2-dimethyl-5-formyl-4-isobutyloxazolidine in 1.0 ml of dry tetrahydrofuran was added thereto, and the mixture was stirred overnight at room temperature.

The reaction mixture was cooled to 0° C. and neutralized with 1N hydrochloric acid. The solution was extracted three times with ethyl acetate. The organic layer was washed sequentially with water and a saturated sodium chloride aqueous solution and then dried over anhydrous sodium sulfate. The solvent was distilled off under reduced pressure, and the residue was purified by silica gel column chromatography (15 g of Kiesel gel 60) by using a mixture of n-hexane/ethyl acetate (10/1) to obtain 518 mg of ethyl 3-[(4S,5S)-3-benzyloxycarbonyl-2,2-dimethyl-4-isobutyloxazolin-5-yl]-2-ethyl-2-propenoate as a colorless oily substance.

$R_f$: 0.53(silica gel plate, developer:
n-hexane/ethyl acetate (5/1))
NMR(60 MHz, CDCl$_3$): δppm: 0.7–1.8(21H, m), 2.32(2H, m), 3.80(1H, m), 4.20(2H, q, J=7 Hz), 4.58(0.5H, dd, J=2, 9 Hz), 5.10(0.5H, m), 5.11(2H, s), 5.85(0.5H, brd, J=9 Hz), 6.66(0.5H, d, J=9 Hz), 7.30(5H, s).

(b) 517 mg of ethyl 3-[(4S,5S)-3-benzyloxycarbonyl-2,2-dimethyl-4-isobutyloxazolidin-5-yl]-2-ethyl-2-propenoate was dissolved in 3.10 ml of an ethanol/water (9/1) solution of 2N potassium hydroxide, and the mixture was stirred for 3 hours at room temperature.

The reaction solution was adjusted to pH 2 with 1N hydrochloric acid under cooling with ice. Then, 24 ml of water was added thereto and extracted three times with 20 ml of ethyl acetate. The organic layer was washed sequentially with water and a saturated sodium chloride aqueous solution, and dried over anhydrous sodium sulfate. The solvent was distilled off under reduced pressure to obtain 3-[(4S,5S)-3-benzyloxycarbonyl-2,2-dimethyl-4-isobutyloxazolidin-5-yl]-2-ethyl-2propenoic acid as a colorless oily substance.

Without purification, the propenoic acid was dissolved in 1.0 ml of dry dimethylformamide, and 145 μl of isobutylamine, 320 μl of diphenylphosphorylazide and 207 μl of triethylamine were added thereto at −10° C. under stirring. The mixture was stirred for 1 hour at −10° C., and further stirred overnight at room temperature, and then, 60 ml of ethyl acetate was added thereto. The organic layer was washed sequentially with a 10% of citric acid aqueous solution, water, a 4% sodium hydrogen carbonate, water and saturated sodium hydrochloride aqueous solution, and dried over anhydrous sodium sulfate. The solvent was distilled off under reduced pressure, and the residue was purified by silica gel column chromatography (65 g of Kiesel gel 60) by using a mixture of n-hexane/ethyl acetate (5/1) to obtain 204 mg of 3-[(4S,5S)-3-benzyloxycarbonyl-2,2-dimethyl-4-isobutyloxazolidin-5-yl]-2-ethyl-2(Z)-propeonoic acid isobutylamide, 151 mg of 3-[(4S,5S)-3-benzyloxycarbonyl-2,2-dimethyl-4-isobutyloxazolidin-5-yl]-2-ethyl-2(E)-propeonoic acid isobutylamide and 55 mg of a mixture thereof as colorless oily substances.

$R_f$: 2(Z)-isomer, 0.37 (silica gel plate, developer: n-hexane/ethyl acetate (5/2))

2(E)-isomer, 0.28 (silica gel plate, developer: n-hexane/ethyl ecetate (5/2))

NMR(60 MHz, CDCl$_3$)

2(Z)-isomer: δppm: 0.7–1.3(15H, m), 1.4–2.1(10H, m), 2.30(2H, m), 3.20(2H, dd, J=6, 6 Hz), 3.8(1H, m), 4.52(1H, dd, J=2, 9 Hz), 5.12(2H, s), 5.60(1H, brd, J=9 Hz), 6.50(1H, m), 7.30(5H, s).

2(E)-isomer: δppm: 0.7–1.3(15H, m), 1.3–2.0(10H, m), 2.30(2H, m), 3.10(2H, dd, J=6, 6 Hz), 3.75(1H, m), 4.52(1H, dd, J=2, 9 Hz), 5.04(2H, s), 5.75(1H, m), 6.00(1H, d, J=9 Hz), 7.25(5H, s).

(3) (4S,5S)-5-(L-N-benzyloxycarbonylnaphthylalanyl-L-norleucyl)amino-4-hydroxy-2-ethyl-7-methyl-2(E)-octenoic acid isobutylamide (a) 85.3 mg of 3-[(4S,5S)-3-benzyloxycarbonyl-2,2-dimethyl-4-isobutyloxazolidin-5-yl]-2-ethyl-2(E)-propenoic acid isobutylamide was dissolved in 0.5 ml of ethanol and hydrogenated by using 10% palladium carbon under atmospheric pressure. The reaction mixture was subjected to filtration, and the solvent was distilled off from the filtrate under reduced pressure to obtain 47 mg of (4S,5S)-5-amino-4-hydroxy-2-ethyl-7-methyl-2(E)-octenoic acid isobutylamide as a colorless oily substance.

$R_f$: 0.27(silica gel plate, developer: chloroform/methanol/aqueous ammonia, (10/0.5/0.2))

(b) 47 mg of (4S,5S)-5-amino-4-hydroxy-2-ethyl-7-methyl-2(E)-octenoic acid isobutylamide was dissolved in 0.5 ml of dry dimethylformamide, and 80 mg of L-N-benzyloxycarbonylnaphthylalanyl-L-norleucine, 45 μl of diphenylphosphorylazide and 29 μl of triethylamine were added thereto at −10° C. under stirring. The mixture was stirred for 1 hour at −10° C. and then stirred overnight at room temperature. 40 ml of ethyl acetate was added to the reaction solution. The organic layer was washed sequentially with a 10% citric acid aqueous solution, water, a 4% sodium hydrogen carbonate aqueous solution, water and a saturated sodium chloride aqueous solution and dried over anhydrous sodium sulfate. The solvent was distilled off under reduced pressure and the residue was purified by silica gel column chromatography (7.5 g of Kiesel gel 60) by using a mixture of chloroform/methanol (40/1) to obtain 59 mg of (4S,5S)-5-(L-N-benzyloxycarbonylnaphthylalanyl-L-norleucyl)amino-4-hydroxy-2-ethyl-7-methyl-2(E)-octenoic acid isobutylamide (Compound B) as a colorless powder.

$R_f$: 0.30(silica gel plate, developer: chloroform/methanol (20/1))

Mass spectrum 715(M$^+$+1)

NMR(300 MHz, CD$_3$OD)

2(E)-isomer: δppm: 0.85–1.03(15H), 1.08(3H, t, J=7.5 Hz) 1.30–1.75(8H), 1.84(2H, m), 2.42(2H, m), 3.04(2H, m), 3.75(1H, dd, J=7, 15 Hz), 4.05(1H, m), 4.28(1H, dd, J=4, 8 Hz), 4.44(1H, dd, J=3, 8 Hz), 4.62(1H, m), 5.04(2H, s), 5.96(1H, s), 7.20–7.48(7H), 7.48–7.63(2H, m), 7.82(1H, m), 7.93(1H, d, J=8 Hz), 8.25(1H, m).

(4) (4S,5S)-5-(L-N-benzyloxycarbonylnaphthylalanyl-L-norleucyl)amino-2-ethyl-4-hydroxy-7-methyl-2(Z)-octenoic acid isobutylamide (a) 64 mg of 3-[(4S,5S)-3-benzyloxycarbonyl-2,2-dimethyl-4-isobutyloxazolidin-5-yl]-2-ethyl-2(Z)-propenoic acid isobutylamide was dissolved in 1.5 ml of methanol, and hydrogenated by using 10% palladium carbon under atmospheric pressure. The reaction mixture was subjected to filtration, and the solvent was distilled off from the filtrate under reduced pressure to obtain 38 mg of (4S,5S)-5-amino-2-ethyl-4-hydroxy-7-methyl-2(Z)-octenoic acid isobutylamide as a colorless oily substance.

$R_f$: 0.33 (silica gel plate, developer: chloroform/methanol/aqueous ammonia, (10/0.5/0.2))

(b) 38 mg of (4S,5S)-5-amino-2-ethyl-4-hydroxy-7-methyl-2(Z)-octenoic acid isobutylamide was dissolved in 0.5 ml of dry dimethylformamide and 66 mg of L-N-benzyloxycarbonylnaphthylalanyl-L-norleucine, 37 μl of diphenylphosphorylazide and 24 μl of triethylamine were added thereto at −10° C. under stirring. The mixture was stirred for 1 hour at −10° C., and then stirred overnight at room temperature. 200 ml of ethyl acetate was added to the reaction solution, and the organic layer was washed sequentially with a 10% citric acid aqueous solution, water a 4% sodium hydrogen carbonate aqueous solution and water and dried over anhydrous sodium sulfate. The solvent was distilled off under reduced pressure and precipitated crystals were collected by filtration to obtain 22 mg of (4S,5S)-5-(L-N-benzyloxycarbonylnaphthylalanyl-L-norleucyl)amino-2-ethyl-4-hydroxy-7-methyl-2(Z)-octenoic acid isobutylamide (Compound C) as a colorless powder.

$R_f$: 0.23 (silica gel plate, developer: chloroform/methanol (20/1))

Mass spectrum m/z 715(M$^+$+1)

NMR(300 MHz, CD$_3$OD)

2(Z)-isomer: δppm: 0.84–1.00(15H), 1.03(3H, t, J=8 Hz), 1.24–1.40(4H), 1.49–1.70(4H), 1.80(2H, m), 2.25(2H, q, J=8 Hz), 3.05(2H, d, J=7 Hz), 3.68(1H, m), 3.96(1H, m), 4.19(1H, dd, J=3, 8 Hz), 4.29(1H, dd, J=4, 8 Hz), 4.55(1H, m), 4.98(2H, s), 5,40(1H, d, J=8 Hz), 7.15–7.40(7H), 7.50(2H, m), 7.76(1H, m), 7.87(1H, d, J=8 Hz), 8.18(1H, d, J=8 Hz)

EXAMPLE 3

(4S,5S)-5-(L-N-benzyloxycarbonylnaphthylalanyl-L-norleucyl)amino-4-hydroxy-7-methyl-2-propyl-2-octenoic acid isobutylamide (1) Ethyl 2-diethylphosphonopentanoate 856 mg of a sodium hydride dispersion (60% in oil) was washed three times with n-hexane under a nitrogen atmosphere to separate the oil. After drying, the powder obtained was suspended in 7.2 ml of dry dimethylformamide under a nitrogen atmosphere, and 4.26 ml of ethyl diethylphosphono acetate was dropwise added over a period of 1 hour at 0° C. under stirring. The mixture was stirred 1 hour at room temperature and then cooled to 0° C. Then, 2.34 ml of 1-bromopropane was added thereto under stirring, and mixture was stirred overnight at 55° C.

The reaction mixture was poured into 40 ml of water and extracted three times with 20 ml of ethyl acetate. The organic layer was washed sequentially with water and a saturated sodium chloride aqueous solution and then dried over anhydrous sodium sulfate. Then, the solvent was distilled off under reduced pressure, and the residue was purified by silica gel column chromatography (120 g of Kiesel gel 60) by using a mixture of n-hexane/acetone (4/1) to obtain 3.47 g of ethyl 2-diethyl phosphonopentanoate as an oily substance.

$R_f$: 0.38 (silica gel plate, developer: n-hexane/ethyl acetate (1/1))

NMR(60 MHz, CDCl$_3$): δppm: 0.7–1.1(3H, m), 1.25(3H, t, J=7 Hz), 1.30(6H, t, J=7 Hz), 1.4–2.2(4H, m), 2.6–3.2(1H, m), 4.05(2H, q, 7 Hz), 4.15(4H, q, J=7 Hz).

Mass sepectrum m/z 267(M$^+$+1).

(2) 3-[(4S,5S)-3-benzyloxycarbonyl-2,2-dimethyl-4-isobutyloxazolidin-5-yl]-2-propyl-2-propeonic acid isobutylamide (a) 71.6 mg of lithium chloride was suspended in 5 ml of dry tetrahydrofuran under an argon atmosphere, and a solution prepared by dissolving 455 mg of ethyl 2-diethylphosphonopentanoate in 0.6 ml of dry tetrahydrofuran, was added thereto under stirring. The mixture was stirred for 5 minutes at room temperature, and then a 50% dry tetrahydrofuran solution containing 323 mg of diazabicycloundecene was added thereto. The mixture was stirred for 10 minutes at room temperature. Then, a solution prepared by dissolving 450 mg of (4S,5R)-3-benzyloxycarbonyl-2,2-dimethyl-5-formyl-4-isobutyloxazoline in 1.0 ml of dry tetrahydrofuran was added thereto, and the mixture was stirred overnight at room temperature.

The reaction solution was cooled to 0° C. and neutralized with 1N hydrochloric acid. The solution was extracted three times with ethyl acetate and the organic layer was washed sequentially with water and a saturated sodium chloride aqueous solution and dried over anhydrous sodium sulfate. The solvent was distilled off under reduced pressure and the residue was purified by silica gel column chromatography, (15 g of Kiesel gel 60) by using a mixture of n-hexane/ethyl acetate (10/1) to obtain 560 mg of ethyl 3-[(4S,5S)-3-benzyloxycarbonyl-2,2-dimethyl-4-isobutyloxazolidin-5-yl]-2-propyl-2-propenoate as a colorless oily substance.

$R_f$: 0.50 (silica gel plate, developer: n-hexane/ethyl acetate (5/1))

Mass spectrum m/z 432 (M$^+$+1)

NMR(60 MHz, CDCl$_3$): δppm: 0.7–1.8(23H), 2.25(2H, m), 3.80(1H, m), 4.20(2H, q, J=7 Hz), 4.60(0.5H, dd, J=2.9 Hz), 5.05(0.5H, m), 5.12(2H, s), 5.85(0.5H, d, J=9 Hz), 6.72(0.5H, d, J=9 Hz), 7.31(5H, s)

(b) 459 mg of ethyl 3-[(4S,5S)-3-benzyloxycarbonyl-2,2-dimethyl-4-isobutyloxazolidin-5-yl]-2-propyl-2-propenoate was dissolved in 2.66 ml of an ethanol/water (9/1) solution of 2N potassium hydroxide and stirred for 4 hours at room temperature.

The reaction mixture was adjusted to pH 2 with 1N hydrochloric acid at 0° C. under stirring. Then, 24 ml of water was added thereto and extracted three times with 20 ml of ethyl acetate. The organic layer was washed sequentially with water and a saturated sodium chloride aqueous solution, and dried over anhydrous sodium sulfate. The solvent was distilled off under reduced pressure to obtain 3-[(4S,5S)-3-benzyloxycarbonyl-2,2-dimethyl-4-isobutyloxazolidin-5-yl]-2-propyl-2-propenoic acid as a colorless oily substnce.

Without purification, the propenoic acid was dissolved in 1.0 ml of dimethylformamide, and 124 μl of isobutylamine, 275 μl of diphenylphosphorylazide and 178 μl of triethylamine were added thereto at −10° C. under stirring. The mixture was stirred 1 hour at −10° C. and then stirred overnight at room temperature. 60 ml of ethyl acetate was added to the reaction solution. The organic layer was washed sequentially with a 10% citric acid aqueous solution, water, a 4% sodium hydrogen carbonate aqueous solution, water and saturated sodium chloride aqueous solution, and dried over anhydrous sodium sulfate. The solvent was distilled off under reduced pressure, and the residue was purified by silica gel column chromatography (60 g of Kiesel gel 60) by using a solvent mixture of n-hexane/ethyl acetate (5/1) to obtain 181 mg of 3-[(4S,5S)-3-benzyloxycarbonyl-2,2-dimethyl-4-isobutyloxazolidin-5-yl]-2-propyl-2(Z)-propeonic acid isobutylamide and 186 mg of 3-[(4S,5S)-3-benzyloxycarbonyl-2,2-dimethyl-4-isobutyloxazolidin-5-yl]-2-propyl-2(E)-propenoic acid isobutylamide as colorless oily substances.

$R_f$: 2(Z)-isomer 0.44, 2(E)-isomer 0.31
(silica gel plate, developer: n-hexane/ethyl acetate (5/2))

NMR (60 MHz, CDCl$_3$)

2(Z)-isomer: δppm: 0.7–1.1(15H), 1.2–2.0(12H), 2.2(2H, m), 3.15(2H, dd, J=6, 6 Hz), 3.75(1H, m), 4.45(1H, dd, J=2, 9 Hz), 5.10(2H, s), 5.60(1H, d, J=9 Hz), 6.50(1H, m), 7.30(5H, s).

2(E)-isomer: δppm: 0.7–1.2(15H), 1.2–2.0(12H), 2.3(2H, m), 3.10(2H, dd, J=6, 6 Hz), 3.85(1H, m), 4.55(1H, dd, J=2, 9 Hz), 5.10(2H, s), 5.75(1H, m), 6.08(1H, d, J=9 Hz), 7.30(5H, s).

(3) (4S,5S)-5-(L-N-benzyloxycarbonylnaphthylalanyl-L-norleucyl)amino-4-hydroxy-2-propyl-7-methyl-2(E)-octenoic acid isobutylamide (a) 85 mg of 3-[(4S,5S)-3-benzyloxycarbonyl-2,2-dimethyl-4-isobutyloxazolidin-5-yl]-2-propyl-2(E)-propenoic acid isobutylamide was dissolved in 1 ml of ethanol, and hydrogenated by using 10% palladium carbon under atmospheric pressure. The rection mixture was subjected to filtration, and the solvent was distilled off from the filtrate under reduced pressure to obtain 53 mg of (4S,5S)-5-amino-4-hydroxy-2-propyl-7-methyl-2(E)-octenoic acid isobutylamide as a colorless oily substance.

$R_f$: 0.18 (silica gel plate, developer:

chloroform/methanol/aqueous ammonia, (10/0.5/0.2))

(b) 53 mg of (4S,5S)-5-amino-4-hydroxy-2-propyl-7-methyl-2(E)-octenoic acid isobutylamide was dissolved in 0.5 ml of dry dimethylformamide, and 85 mg of L-N-benzyloxycarbonylnaphthylalanyl-L-norleucine, 48 μl of diphenylphosphorylazide and 31 μl of triethylamine were added thereto at −10° C. under stirring. The mixture was stirred 1 hour at −10° C., and then stirred overnight at room temperature. Then, 40 ml of ethyl acetate was added to the reaction solution. The organic layer was washed sequentially with a 10% citric acid aqueous solution, water, a 4% sodium hydrogen carbonate aqueous solution, water and a saturated sodium chloride aqueous solution, and dried over anhydrous sodium sulfate. The solvent was distilled off under reduced pressure, and the residue was purified by silica gel column chromatography (10 g of Kiesel gel 60) by using a mixture of chloroform/methanol (40/1) to obtain 46 mg of (4S,5S)-5-(L-N-benzyloxycarbonylnaphthylalanyl-L-norleucyl)-amino-4-hydroxy-2-propyl-7-methyl-2(E)-octenoic acid isobutylamide (Compound D) as a colorless powder.

$R_f$: 0.37(silica gel plate, developer: chloroform/methanol (20/1))
Mass spectrum m/z 728(M+)
NMR (300 MHz, CD$_3$OD)
2(E)-isomer: δppm: 0.83–1.02(18H), 1.34–1.50(6H), 1.50–1.73(4H, 1.73–1.88(2H), 2.35(2H, m), 3.00(2H, m), 3.70(1H, dd, J=6.8, 15 Hz), 4.00(1H, m), 4.24(1H, m), 4.40(1H, dd, J=4, 8 Hz), 5.00(2H, s), 5.95(1H, d, J=8 Hz), 7.19–7.45(7H), 7.45–7.60(2H), 7.78(1H, m), 7.90(1H, d, J=8 Hz), 8.20(1H, d, J=8 Hz).

(4) (4S,5S)-5-(L-N-benzyloxycarbonylnaphthylalanyl-L-norleucyl)amino-4-hydroxy-2-propyl-7-methyl-2(Z)-octenoic acid isobutylamide (a) 71 mg of 3-[(4S,5S)-3-benzyloxycarbonyl-2,2-dimethyl-4-isobutyloxazolidin-5-yl]-2-propyl-2(Z)-propenoic acid isobutylamide was dissolved in 1 ml of ethanol, and hydrogenated by 10% palladium carbon under atmospheric pressure. The reaction mixture was subjected to filtration, and the solvent was distilled off from the filtrate under reduced pressure to obtain 31 mg of (4S,5S)-5-amino-4-hydroxy-2-propyl-7-methyl-2(Z)-octenoic acid isobtylamide as a colorless oily substance.

$R_f$: 0.25 (silica gel plate, developer: chloroform/methanol/aqueous ammonia, (10/0.5/0.2)

(b) 31 mg of (4S,5S)-5-amino-4-hydroxy-2-propyl-7-methyl-2(Z)-octenoic acid isobutylamide was dissolved in 0.3 ml of dry dimethylformamide, and 50 mg of L-N-benzyloxycarbonylnaphthylalanyl-L-norleucine, 28 μl of diphenylphosphorylazide and 18 μl of triethylamine were added thereto at −10° C. under stirring. The mixture was stirred for 1 hour at −10° C., and further stirred overnight at room temperature. Precipitates formed were collected by filtration and washed with methanol to obtain 19 mg of (4S,5S)-5-(L-N-benzyloxycarbonylnaphthylalanyl-L-norleucyl)amino-4-hydroxy-2-propyl-7-methyl-2(Z)-octenoic acid isobutylamide (Compound E) as a colorless powder.

$R_f$: 0.36 (silica gel plate, developer: chloroform/methanol (20/1))
Mass spectrum m/z 729(M+ +1)
NMR(300 MHz, CD$_3$OD)
2(Z)-isomer: δppm: 0.85–1.00(18H), 1.23–1.72(10H), 1.80(2H, m), 2.20(2H, m), 3.05(2H, d, J=7 Hz), 3.68(1H, m), 3.96(1H, m), 4.18(1H, dd, J=4, 8 Hz), 4.30(1H, m), 4.55(1H, m), 4.95(2H, s), 5.40(1H, d, J=8 Hz), 7.16–7.43(7H), 7.43–7.60(2H), 7.76(1H, m), 7.87(1H, d, J=8 Hz), 8.20(1H, d, J=8 Hz).

EXAMPLE 4

(4S,5S)-5-(L-N-benzyloxycarbonylnaphthylalanyl-L-norleucyl)amino-4-hydroxy-2-isopropyl-7-methyl-2-octenoic acid isobutylamide (1) Ethyl 2-diethylphosphono-3-methylbutanoate 428 mg of a sodium hydride dispersion (60% in oil) was washed three times with n-hexane under a nitrogen atmosphere to separate the oil. After drying, the powder obtained was suspended in 3 ml of dry dimethylformamide under a nitrogen atmosphere, and 1.77 ml of ethyl diethylphosphono acetate was dropwise added over a period of 15 minute at 0° C. under stirring. The mixture was stirred for 30 minutes at room temperature, and then cooled to 0° C. Then, 2.52 ml of 2-bromopropane was added thereto under stirring and the mixture was stirred for 30 minutes at room temperature. The mixture was further stirred 5 hours at 65° C. and stirred overnight at room temperature. The reaction solution was poured into 2N hydrochloric acid and extracted three times with 10 ml of chloroform. The chloroform layers were put together and dried over anhydrous magnesium sulfate. The solvent was distilled off under reduced pressure, and the residue was purified by silica gel column chromatography (20 g of Kiesel gel 60) by using a mixture of n-hexane/ethyl acetate (2/1) to obtain 1.33 g of ethyl 2-diethylphosphono-3-methylbutanoate as a colorless oily substance.

$R_f$: 0.50 (silica gel plate, developer: n-hexane/ethyl acetate (1/3))
Mass spectrum 267 (M+ +1)
NMR (60 MHz, CDCl$_3$): δppm: 0.91−1.2(6H, m), 1.28(3H, t, J=7.2 Hz), 1.30(6H, t, J=7.2 Hz), 2.08–2.97(2H, m), 4.11(dq, J=7.2 Hz), 4.18(q, J=7.2 Hz).

(2) 3-[(4S,5S)-3-benzyloxycarbonyl-2,2-dimethyl-4-isobutyloxazolidin-5-yl]-2-isopropyl-2-propenoic acid isobutylamide (a) 123 mg of lithium chloride was suspended in 10 ml of dry tetrahydrofuran under an argon atmosphere, and 0.69 ml of ethyl 2-diethylphosphono-3-methylbutanoate was added thereto under stirring. Then, 2.7 ml of a 20% dry tetrahydrofuran solution of diazabicycloundecene was added thereto and stirred for 10 minutes at room temperature. A solution prepared by dissolving 773 mg of (4S,5R)-3-benzyloxycarbonyl-2,2-dimethyl-5-formyl-4-isobutyloxazolidine in dry tetrahydrofuran was gradually dropwise added thereto, and the mixture was stirred overnight at room temperature. The inorganic salt precipitated was filtered off and the solvent was distilled off under reduced pressure. The residue was dissolved in 300 ml of benzene, washed with water and dried oer anhydrous magnesium sulfate. The solvent was distilled off under reduced pressure, and the residue was purified by silica gel column chromatography (32 g of Kiesel gel 60) by using a mixture of n-hexane/ethyl acetate (10/1) to obtain 623 mg of ethyl 3-[(4S,5S)-3-benzyloxycarbonyl-2,2-dimethyl-4-isobutyloxazolidin-5-yl]-2-isopropyl-2-propenoate as a colorless oily substance.

$R_f$: 0.31 (silica gel plate, developer: benzene/ethyl acetate (30/1))

Mass spectrum m/z 432 (M++1), 416(M+.—CH₃)

NMR (60 MHz), CDCl₃): δppm: 0.60–0.95(6H), 1.02(6H, d, J=9 Hz), 1.25(3H, t, J=9 Hz), 1.50(3H, s), 1.60(3H, s), 1.5–1.8(3H, m), 2.66(1H, m, J=1, 9 Hz), 3.72(1H, m), 4.18(2H, q, J=9 Hz), 4.2(0.3H, m), 4.85(0.7H, dd, J=4, 8.5 Hz), 5.10(2H, s), 5.69(0.7H, dd, J=1, 8.5 Hz), 6.48(0.3H, d, J=8 Hz), 7.28(5H, s).

(b) 400 mg of ethyl 3-[(4S,5S)-3-benzyloxycarbonyl-2,2-dimethyl-4-isobutyloxazolidin-5-yl]-2-isopropyl-2-propenoate was dissolved in 0.2 ml of ethanol and 2.32 ml of an ethanol/water (10/1) solution of 2N potassium hydroxide was added thereto. The mixture was stirred at room temperature for 3 hours and further stirred for 1 hour at 55° C. 24 ml of water was added to the reaction solution, and the reaction solution was adjusted to pH 2 with 1N hydrochloric acid under cooling with ice. The solution was extracted three times with ethyl acetate, and the organic layer was washed with sequentially water and a saturated sodium chloride aqueous solution and dried over anhydrous sodium sulfate. The solvent was distilled off under reduced pressure to obtain 375 mg of 3-[(4S,5S)-3-benzyloxycarbonyl-2,2-dimethyl-4-isobutyloxazolidin-5-yl]-2-isopropyl-2-propenoic acid as a colorless oily substance.

Without purification, the propenoic acid was dissolved in 1 ml of dry dimethylformamide, and 109 μl of isobutylamine, 241 μl of diphenylphosphorylazide and 156 μl of triethylamine were added thereto at −10° C. under stirring. The mixture was stirred for 1 hour at −10° C. and further stirred overnight at room temperature. 62 ml of ethyl acetate was added to the reaction solution. The organic layer was washed sequentially with a 10% citric acid aqueous solution, water, a 4% sodium hydrogen carbonate aqueous solution, water and a saturated sodium chloride aqueous solution and dried over anhydrous sodium sulfate. The solvent was distilled off under reduced pressure, and the residue was purified by silica gel column chromatography (48 g of Kiesel gel 60) by using a mixture of n-hexane/ethyl acetate (5/1) to obtain 174 mg of 3-[(4S,5S)-3-benzyloxycarbonyl-2,2-dimethyl-4-isobutyloxazolidin-5-yl]-2-isopropyl-2(Z)-propenoic acid isobutylamide and 18 mg of 3-[(4S,5S)-3-benzyloxycarbonyl-2,2-dimethyl-4-isobutyloxazolidin-5-yl]-2-isopropyl-2(E)-propenoic acid isobutylamide as colorless oily substances.

R$_f$: 2(Z)-isomer: 0.37, 2(E)-isomer: 0.31
(silica gel plate, developer: n-hexane/ethyl acetate (5/2))

NMR: 2(Z)-isomer (60 MHz, CDCl₃); 2(E)-isomer (300 MHz, CDCl₃).

2(Z)-isomer δppm: 0.75–0.95(6H, br),0.95(6H, d, J=7 Hz), 1.05(3H, d, J=7.5 Hz), 1.08(3H, d, J=7.5 Hz), 1.50(3H, s), 1.60(3H, s), 1.5–2.1(4H, m), 2.75(1H, m, J=1.5, 7 Hz), 3.20(2H, dd, J=6.5, 6.5 Hz), 3.85(1H, m), 4.45(1H, dd, J=3, 9 Hz), 5.10(2H, s), 6.38(1H, br), 7.30(5H, s).

2(E)-isomer δppm: 0.75–0.85(3H, br), 0.9(6H, d, J=6.8 Hz), 1.19(6H, d, J=7 Hz), 1.50(3H, s), 1.55(6H, br s), 1.55–1.65(3H, br), 1.78(1H, m, J=6, 8 Hz), 2.89(1H, m, J=1 Hz), 3.08(2H, dd, J=7.3, 7.3 Hz), 3.79(1H, br), 4.63(1H, dd, J=3.6, 9 Hz), 5.06(1H, brd, J=13.2 Hz), 5.17(1H, d, J=13.2 Hz), 5.68(1H, br), 5.70(1H, d, J=9 Hz), 7.35(5H, s).

(3) (4S,5S)-5-(L-N-benzyloxycarbonylnaphthylalanyl-L-norleucyl)amino-4-hydroxy-2-isopropyl-7-methyl-2(E)-octenoic acid isobutylamide (a) 15.7 mg of 3-[(4S,5S)-3-benzyloxycarbonyl-2,2-dimethyl-4-isobutyloxazolidin-5-yl]-2-isopropyl-2(E)-propenoic acid isobutylamide was dissolved in 0.5 ml of ethanol and hydrogenated by using palladium black under atmospheric pressure. The reaction mixture was subjected to filtration and the solvent was distilled off from the filtrate under reduced pressure to obtain 9 mg of (4S,5S)-5-amino-4-hydroxy-2-isopropyl-7-methyl-2(E)-octenoic acid isobutylamide as a colorless oily substance.

R$_f$: 0.28 (silica gel plate, developer: chloroform/methanol/aqueous ammonia (10/1/0.2))

(b) 9 mg of (4S,5S)-5-amino-4-hydroxy-2-isopropyl-7-methyl-2(E)-octenoic acid isobutylamide was dissolved in 0.5 ml of dry dimethylformamide, and 13 mg of L-N-benzyloxycarbonylnaphthylalanyl-L-norleucine, 8.8 μl of diphenylphosphorylazide and 5.7 μl of triethylamine were added thereto at −10° C. under stirring. The mixture was stirred for 1 hour at −10° C. and further stirred overnight at room temperature. 6 ml of ethyl acetate was added to the reaction solution, and the organic layer was washed sequentially with a 10% citric acid aqueous solution, water, a 4% sodium hydrogen carbonate aqueous solution, water and a saturated sodium chloride aqueous solution, and dried over anhydrous sodium sulfate. The solvent was distilled off under reduced pressure, and the residue was purified by silica gel column chromatography (4 g of Kiesel gel 60) by using a mixture of chloroform/ethyl acetate (5/2) to obtain 8 mg of (4S,5S)-5-(L-N-benzyloxycarbonylnaphthylalanyl-L-norleucyl)amino-4-hydroxy-2-isopropyl-7-methyl-2(E)-octenoic acid isobutylamide (Compound F) as a colorless powder.

R$_f$: 0.26 (silica gel plate, developer: chloroform/methanol (20/1))

Mass spectrum m/z 729(M++1)

NMR (300 MHz, CDCl₃): δppm: 0.74–0.95(15H), 1.05–1.31(10H) 1.31–1.58(4H), 1.58–1.83(2H), 3.74(1H, m, J=7.4 Hz), 3.0(2H, m), 3.36(1H, m), 3.55(1H, m), 3.85(1H, m), 4.15(1H, m), 4.33(1H, dd, J=2.6, 9.5 Hz), 4.50(1H, m), 4.97(2H, s), 5.41(1H, d, J=9.5 Hz), 7.24–7.40(7H, m), 7.40–7.57(2H, m), 7.72(1H, d, J=8 Hz), 7.81(1H, d, J=8 Hz), 8.07(1H, d, H=8 Hz).

(4) (4S,5S)-5-(L-N-benzyloxycarbonylnaphthylalanyl-L-norleucyl)amino-4-hydroxy-2-isopropyl-7-methyl-2(Z)-octenoic acid isobutylamide (a) 127 mg of 3-[(4S,5S)-3-benzyloxycarbonyl-2,2-dimethyl-4-isobutyloxazolidin-5-yl]-2-isopropyl-2(Z)-propenoic acid isobutylamide was dissolved in 2.5 ml of ethanol, and hydrogenated by using 10% palladium carbon under atmospheric pressure. The reaction mixture was subjected to filtration and the solvent was distilled off from the filtrated under reduced pressure to obtain 78 mg of (4S,5S)-5-amino-4-hydroxy-2-isopropyl-7-methyl-2(Z)-octenoic acid isobutylamide as a colorless oily substance.

R$_f$: 0.67 (silica gel plate, developer: chloroform/methanol/aqeuous ammonia (10/2/0.2))

(b) 78 mg of (4S,5S)-5-amino-4-hydroxy-2-isopropyl-7-methyl-2(Z)-octenoic acid isobutylamide was dissolved in 2 ml of dry dimethylformamide, and 128 mg of L-N-benzyloxycarbonylnaphthylalanyl-L-norleucine, 72 μl of diphenylphosphorylazide and 46 μl of triethylamine were added thereto at −10° C. under stirring. The mixture was stirred for 1 hour at −10° C. and further stirred overnight at room temperature. Precipitates formed in the reaction solution were collected by filtration to obtain 37 mg of (4S,5S)-5-(L-N-benzyloxycarbonylnaphthylalanyl-L-norleucyl)amino-4- hydroxy-2-isopropyl-7-methyl-2(Z)-octenoic acid isobutylamide (Compound G) as a colorless powder.

R$_f$: 0.50 (silica gel plate, developer: chloroform/methanol (20/1))

Mass spectrum m/z 729(M$^+$+1)

NMR(300 MHz, CD$_3$OD): δppm: 0.82–0.96(15H), 1.04(3H, d, J=6.8 Hz), 1.05(3H, d, J=6.8 Hz), 1.28(6H, br), 1.54(3H, m), 1.79(1H, m, J=6.8 Hz), 2.49(1H, m, J=1.5, 6.8 Hz), 3.05(2H, m), 3.65(1H, dd, J=5.1, 13.7 Hz), 3.90(1H, m), 4.10(1H, dd, J=3.8, 9.0 Hz), 4.25(1H, m), 4.52(2H, s), 5.31(1H, dd, J=1.5, 9 Hz), 7.15–7.35(7H, m), 7.47(1H, m), 7.73(1H, m), 7.83(1H, brd, J=8 Hz), 8.14(2H, d, J=8 Hz)

EXAMPLE 5

(4S,5S)-5-(L-N-benzyloxycarbonylnaphthylalanyl-L-norleucyl)amino-4-hydroxy-2-(2-hydroxyethyl)-7-methyl-2(E)-octenoic acid isobutylamide (a) 216 mg of 3-[(4S,5S)-3-benzyloxycarbonyl-2,2-dimethyl-4-isobutyloxazolidin-5-yl]-2-[2-(2-tetrahydropyranyloxy)ethyl]-2-propenoic acid isobutylamide was dissolved in 2.1 ml of ethanol, and hydrogenated by using 10% palladium carbon under atmospheric pressure. The reaction mixture was subjected to filtration, and the solvent was distilled off from the filtrate under reduced pressure to obtain 124 mg of (4S,5S)-5-amino-4-hydroxy-2-[2-(2-tetrahydropyranyloxy)ethyl]-7-methyl-2-octenoic acid isobutylamide as a colorless oily substance.

R$_f$: 0.29 (silica gel plate, developer: chloroform/methanol/aqeuous ammonia, (10/0.5/0.2))

(b) 124 mg of (4S,5S)-5-amino-4-hydroxy-2-[2-(2-tetrahydropyranyloxy)ethyl]-7-methyl-2-octenoic acid isobutylamide was dissolved in 1 ml of dry dimethylformamide, and 154 mg of L-N-benzyloxycarbonylnaphthylalanyl-L-norleucine, 87 μl of diphenylphosphorylazide and 56 μl of triethylamine were added thereto at −10° C. under stirring. The mixture was stirred for 1 hour at −10° C., and further stirred overnight at room temperature. 100 ml of ethyl acetate waa added to the reaction solution. The organic layer was washed sequentially with a 10% citric acid aqueous solution, water, a 4% sodium hydrogen carbonate aqueous solution, water, and a saturated sodium chloride aqueous solution, and dried over anhydrous sodium sulfate. The solvent was distilled off under reduced pressure, and the residue was prurified by silica gel column chromatography (10 g of Kiesel gel 60) by using a mixture of chloroform/methanol (40/1) to obtain 116 mg of (4S,5S)-5-(L-N-benzyloxycarbonylnaphthylalanyl-L-norleucyl)amino-4-hydroxy-2-[2-(2-tetrahydropyranyloxy)ethyl]-7-methyl-2-octenoic acid isobutylamide as a colorless oily substance.

R$_f$: 0.51 (silica gel plate, developer: chloroform/methanol (20/1))

Mass spectrum m/z 816(M$^+$+1)

NMR(60 MHz, CDCl$_3$+CD$_3$OD): δppm: 0.7–1.1(15H), 1.1–1.2(16H), 2.7(2H, m), 3.0(2H, m), 3.2–4.5(11H, m), 5.0(2H, s), 5.55(0.5H, d, J=8 Hz), 6.05(0.5H, d, J=8 Hz), 7.0–8.3(12H).

(c) 113 mg of (4S,5S)-5-(L-N-benzyloxycarbonylnaphthylalanyl-L-norleucyl)amino-4-hydroxy-2-[2-(2-tetrahydropyranyloxy)ethyl]-7-methyl-2-ocetenoic acid isobutylamide was dissolved in a solvent mixture of methanol/ethyl acetate/chloroform (1.6 ml/1.6 ml/0.5 ml), and 0.41 ml of 1N hydrochloric acid was added thereto. After stirring for 2 hours at room temperature, 15 ml of water was added thereto, and extracted once with 30 ml of ethyl acetate and extracted twice with 15 ml of ethyl acetate. The organic layer was washed sequentially with water and a saturated sodium chloride aqueous solution, and dried over anhydrous sodium sulfate. The solvent was distilled off under reduced pressure, and the residue was purified by silica gel column chromatography (10 g of Kiesel gel 60) by using a mixture of chloroform/methanol (40/1) to obtain 58 mg of (4S,5S)-5-(L-N-benzyloxycarbonylnaphthylalanyl-L-norleucyl)amino-4-hydroxy-2-(2-hydroxyethyl)-7-methyl-2(E)-octenoic acid isobutylamide as a colorless powder.

R$_f$: 0.24 (silica gel plate, developer: chloroform/methanol (20/1))

Mass spectrum m/z 731 (M$^+$+1)

NMR(60 MHz, CD$_3$OD+CDCl$_3$): δppm: 0.7–1.1(15H), 1.1–2.0(10H), 2.6(2H, m), 3.0(2H, m), 3.3–4.7(8H), 5.0(2H, s), 6.0(2H, d, J=8 Hz), 7.1–8.2(12H).

EXAMPLE 6

(4S,5S)-5-(L-N-benzyloxycarbonylnaphthylalanyl-L-norleucyl)amino-4-hydroxy-2-(3-hydroxpropyl)-7-methyl-2(E)-octenoic acid isobutylamide (1) (4S,5S)-5-(N-benzyloxycarbonyl)amino-4-hydroxy-2-(3-hydroxypropyl)-7-methyl-2-octenoic acid isobutylamide 163 mg of 3-[(4S,5S)-3-benzyloxycarbonyl-2,2-dimethyl-4-isobutyloxazolidin-5-yl]-2-[3-(2-tetrahydropyranyloxy)-propyl]-2-propenoic acid isobutylamide was dissolved in 5.6 ml of dioxane, and 2.8 ml of 1N hydrochloric acid was added thereto. After stirring for 2 hours at room temperature, 10 ml of water was added thereto and extracted three times with ethyl acetate. The ethyl acetate layer was washed sequentially with a 4% sodium hydrogen carbonate aqueous solution, water and a saturated sodium chloride aqueous solution, and dried over anhydrous magnesium sulfate. The solvent was distilled off under reduced pressure, and the residue was purified silica gel column chromatography (4 g of Kiesel gel 60) by using n-hexane/ethyl acetate (1/5) to obtain 64 mg of the above-identified compound.

R$_f$: 0.27 (silica gel plate, developer: n-hexane/ethyl acetate (1/5))

(2) (4S,5S)-5-(L-N-benzyloxycarbonylnaphthylalanyl-L-norleucyl)-amino-4-hydroxy-2-(3-hydroxypropyl)-7-methyl-2(E)-octenoic acid isobutylamide (Compound H)

(a) 61 mg of (4S,5S)-5-(N-benzyloxycarbonyl)amino-4-hydroxy-2-(3-hydroxypropyl)-7-methyl-2-octenoic acid isobutylamide was dissolved in 2.0 ml of ethanol, and hydrogenated by using 10% palladium carbon under atmospheric pressure. The reaction mixture was subjected to filtration, and the solvent was distilled off from the filtrate under reduced pressure. The residue was purified by silica gel column chromatography (1.5 g of Kiesel 60) by using chloroform/methanol/aqueous ammonia (10/1/0.1) to obtain 24.7 mg of (4S,5S)-5-amino-4-hydroxy-2-(3-hydroxypropyl)-7-methyl-2(E)-octenoic acid isobutylamide as a colorless oily substance.

R$_f$: 0.11 (silica gel plate, developer: chloroform/methanol/aqueous ammonia, (10/1/0.1))

(b) 38 mg of L-N-benzyloxycarbonylnaphthylalanyl-L-norleucine was dissolved in 0.3 ml of dry dimethylformamide. Then, 13.8 μl of triethylamine and 0.2 ml of a dry dimethylformamide solution of 22.5 μl of diphenylphosphorylazide and 24.7 mg of (4S,5S)-5-amino-4-hydroxy-2-(3-hydroxypropyl)-7-methyl-2(E)-octenoic acid isobutylamide were added thereto at −20° C. under stirring. The mixture was stirred for 1 hour at −20° C. and further stirred overnight at room temperature. Then, 25 ml of ethyl acetate was added thereto. The ethyl acetate layer was washed sequentially with a 10% citric acid aqueous solution, water, a 4% sodium hydrogen carbonate aqueous solution, water, a saturated sodium chloride aqueous solution, and dried over anhydrous magnesium sulfate. The solvent was distilled off under reduced pressure, and the residue was purified by silica gel column chromatography (3 g of Kiesel gel 60) by using chloroform/methanol (40/1) to obtain 12.7 mg of the above-identified compound as a white powder.

$R_f$: 0.21 (silica gel plate, developer:
chloroform/methanol (10/1))
Mass spectrum m/z 745(M$^+$+1)

EXAMPLE 7

(4S,5S)-5-(L-naphthylalanyl-L-norleucyl)amino-2-ethyl-4-hydroxy-7-methyl-2(E)-octenoic acid isobutylamide monohydrochloride 23.3 mg of (4S,5S)-5-(L-N-benzyloxycarbonylnaphthylalanyl-L-norleucyl)amino-2-ethyl-4-hydroxy-7-methyl-2(E)-octenoic acid isobutylamide was dissolved in 3.0 ml of methanol, and hydrogenated by using 3 mg of 10% palladium carbon as catalyst at room temperature under atmospheric pressure. After the catalyst was filtered off, the solvent was distilled off under reduced pressure. The residue thereby obtained was dissolved in 1.0 ml of methanol and 0.3 ml of 0.1N hydrochloric acid was added thereto. Then, the solvent was distilled off under reduced pressure, and ethyl ether was added to the residue to obtain 19.6 mg of the above-identified compound as a white powder.

$R_f$: 0.50 (silica gel plate, developer:
chloroform/methanol (20/1))
Mass spectrum m/z 581 (M$^+$+1)

Example 8

(4S,5S)-5-(L-N-benzyloxycarbonylnaphthylalanyl-L-norleucyl)amino-1,4-dihydroxy-2-(2-hydroxyethyl)-7-methyl-2-octene (1) (4S,5S)-5-tert-butoxycarbonylamino-1,4-dihydroxy-2-[2-(2-tetrahydropyranyloxy)ethyl]-2(E)-octene (a) 110 mg of ethyl 3-[(4S,5S)-3-benzyloxycarbonyl-2,2-dimethyl-4-isobutyloxazolidin-5-yl]-2-[2-(2-tetrahydropyranyloxy)ethyl]-2-propenoate was dissolved in 1.0 ml of ethanol, and hydrogenated by using 12 mg of 10% palladium carbon as catalyst at room temperature under atmospheric pressure. The catalyst was filtered off, and the solvent was distilled off under reduced pressure to obtain 77 mg of ethyl (4S,5S)-5-amino-4-hydroxy-2-[2-(2-tetrahydropyranyloxy)ethyl]-7-methyl-2-octenoate as a colorless oily substance.

$R_f$:0.37 (silica gel plate, developer:
chloroform/methanol/aqueous ammonia (10/1/0.2))

(b) 77 mg of ethyl (4S,5S)-5-amino-4-hydroxy-2-[2-(2-tetrahydropyranyloxy)ethyl]-7-methyl-2-octenoate was dissolved in 1.0 ml of dimethylformamide, and 33 μl of triethylamine and 60 μl of di-t-butyl dicarbonate were added thereto. The mixture was stirred for 2 hours at room temperature. The reaction solution was poured into 10 ml of water and extracted with ethyl acetate. The ethyl acetate layer was washed sequentially with water and a saturated sodium chloride aqueous solution, and dried over anhydrous magnesium sulfate. The solvent was distilled off under reduced pressure, and the residue was purified by the silica gel column chromatography (3 g of Kiesel gel 60) by using n-hexane/ethyl acetate (10/1) to obtain 16 mg of ethyl (4S,5S)-5-tert-butoxycarbonylamino-4-hydroxy-2-[2-(2-tetrahydropyranyloxy)ethyl]-7-methyl-2-octenoate as a colorless oily substance.

$R_f$: 0.56 (silica gel plate, developer:
n-hexane/ethyl acetate (3/1))

(c) 16 mg of ethyl (4S,5S)-5-tert-butoxycarbonylamino-4-hydroxy-2-[2-(2-tetrahydropyranyloxy)ethyl]-7-methyl-2-octenoate was dissolved in 0.5 ml of dichloromethane, and 13 μl of boron trifluoride ethyl ether complex was added thereto as −78° C. under stirring. The mixture was stirred for 30 minutes at the same temperature. Then, 75 μl of a 1.5M isobutyl aluminum hydride toluene solution was added to the mixture and further stirred for 45 minutes. 60 μl of a 5M acetic acid dichloromethane solution was added thereto at −78° C., and the reaction solution was raised to room temperature. 10 ml of 10% citric acid aqueous solution was added thereto and extracted with ethyl acetate. The extract was washed sequentially with water and a saturated sodium chloride aqueous solution and dried over anhydrous magnesium sulfate. The solvent was distilled off under reduced pressure to obtain 15 mg of (4S,5S)-5-tert-butoxycarbonylamino-1,4-dihydroxy-2-[2-(2-tetrahydropyranyloxy)ethyl]-7-methyl-2-octene as a colorless oily substance.

$R_f$: 0.10 (silica gel plate, developer:
n-hexane/ethyl acetate (3/1))

(2) (4S,5S)-5-(L-N-benzyloxycarbonylnaphthylalanyl-L-norleucyl)amino-1,4-dihydroxy-2-(2-hydroxyethyl)-7-methyl-2-octene.

15 mg of (4S,5S)-5-tert-butoxycarbonylamino-1,4-dihydroxy-2-[2-(2-tetrahydropyranyloxy)ethyl]-7-methyl-2-octene was dissolved in 0.2 ml of 3.6M hydrochloric acid/dioxane, and allowed to stand for 2 hours at 0° C. The solvent was distilled off under reduced pressure to obtain 11 mg of the deprotected product as a colorless oily substance. Without purification, the deprotected product was dissolved in 0.25 ml of dry dimethylformamide, and 0.3 ml of dry dimethylformamide solution containing 13 mg of L-N-benzyloxycarbonylaminonaphthylalanyl-L-norleucine, 10 μl of triethylamine and 10 μl of diphenylphosphorylazide was added thereto. Then, the mixture was stirred for 2 hours at −15° C. and further stirred overnight at room temperature. 20 ml of ethyl acetate was added to the reaction solution, and washed sequentially with a 10% citric acid aqueous solution, water, a 4% sodium hydrogen carbonate aqueous solution, water and a saturated sodium chloride aqueous solution, and dried over anhydrous magnesium sulfate. The solvent was distilled off under reduced pressure, and the residue was purified by silica gel column chromatography (1 g of Kiesel gel 60) by using chloroform/methanol (30/1) to obtain 5.5 mg of (4S,5S)-5-(L-N-benzyloxycarbonylnaphthylalanyl-L-norleucyl)amino-1,4-dihydroxy-2-(2-hydroxyethyl)-7-methyl-2-octene as a white powder.

$R_f$: 0.25 (silica gel plate, developer:
chloroform/methanol (20/1))
Mass spectrum m/z 684 (M$^+$ +Na), 644 (M$^+$+1−H$_2$O)

NMR(300 MHz, CDCl₃); δ ppm: 0.66–0.99(9H, m), 0.99–1.90(9H, m), 2.22–2.63(2H, m), 3.35–3.68(4H, m), 3.75–3.90(1H, m), 3.90–4.32(4H, m), 4.42–4.67(2H, m), 5.04(2H, s), 6.01(0.3H, d, J=9 Hz), 6.18(0.7H, d, J=9 Hz), 7.12–7.42(7H, m), 7.42–7.65(2H, m), 7.78(1H, d, J=8 Hz), 7.85(1H, d, J=8 Hz), 8.15(1H, bd, J=8 Hz).

EXAMPLE 9

(4S,5S)-5-(L-N-benzyloxycarbonylnaphthylalanyl-L-norleucyl)amino-6-cyclohexyl-2-ethyl-4-hydroxy-2(E)-hexenoic acid isobutylamide (1) L-N-benzyloxycarbonylcyclohexylalanine 3,5-dimethylpyrazolide (a) 2 g of L-phenylalanine was dissolved in 30 ml of a 50% of acetic acid, and hydrogenated by using 200 mg of platinum as catalyst under elevated pressure (hydrogen pressure: 50 kg/cm²) for 2 hours at a temperature from 40° to 70° C. The catalyst was filtered off and the solvent was distilled off under reduced pressured to obtain 2.2 g of L-cyclohexylalanine as a colorless needle crystal.

(b) 2.2 g of L-cyclohexylalanine was suspended in 8 ml of water and dissolved by an addition of 2.7 ml of triethylamine. Then, 8 ml of dioxane solution containing 4.2 g of 5-(benzyloxycarbonyl)-4,6-dimethyl-2-thiopyridine was added thereto and stirred for 2 hours at room temperature. 100 ml of water was added to the reaction mixture and extracted with ethyl acetate. The aqueous layer was adjusted to pH 2 with 6N hydrochloric acid under cooling with ice and further extracted with ethyl acetate. The ethyl acetate layer was washed sequentially with 1N hydrochloric acid and a saturated sodium hydrochloride aqueous slution and dried over anhydrous magnesium sulfate. The solvent was distilled off under reduced pressure to obtain 4.1 g of L-N-benzyloxycarbonyl cyclohexylalanine as a colorless oily substance.

R$_f$: 0.48 (silica gel plate, developer: benzene/methanol/acetate (10/1/0.5))

(c) 2 g of L-N-benzyloxycarbonylcyclohexylalanine was dissolved in 20 ml of dichloromethane, and 0.84 g of 3,5-dimethylpyrazole was added thereto. 1.8 g of dicyclohexylcarbodiimide was added thereto under cooling with ice and stirred overnight at a temperature from 0° to 8° C. Precipitates were filtered off and the sovlent was distilled off under reduced pressure. The residue was dissolved in ethyl acetate, washed sequentially with a 10% citric acid aqueous solution, water, a 4% sodium hydrogen carbonate aqueous solution, water, and a saturated sodium chloride aqueous solution and dried over anhydrous magnesium sulfate. The solvent was distilled under reduced pressure, and the residue was crystallized from diethyl ether/n-hexane to obtain 2.1 g of L-N-benzyloxycarbonylcyclohexylalanine 3,5-dimethylpyrazolide as a colorless needle crystal.

Melting point: 93°–94° C.
R$_f$: 0.45 (silica gel plate, developer: n-hexane/ethyl acetate (3/1))

(2) (3RS,4S)-N-benzyloxycarbonyl)-4-amino-5-cyclohexyl-3-hydroxy-1-pentene (a) 792 mg of lithium aluminum hydride was suspended in 50 ml of dry tetrahydrofuran, and a solution prepared by dissolving 4 g of L-N-benzyloxycarbonylcyclohexylalanine 3,5-dimethylpyrazolide in 50 ml of dry tetrahydrofuran was dropwise added thereto at a temperature from −40° to −45° C. under an argon stream over a period of about 40 minutes. The mixture was stirred for 20 minutes at the same temperature and then 5 ml of 5N hydrochloric acid was added thereto. Insolubles were filtered off and the solvent was distilled off under reduced pressure. The residue was dissolved in ethyl acetate and the ethyl acetate layer was washed sequentially with 1N hydrochloride acid and a saturated sodium chloride aqueous solution, and dried over anhydrous magnesium sulfate. The solvent was distlled off under reduced pressure to obtain 3.4 g of L-N-benzyloxycarbonylcyclohexylalaninal as a colorless oily substance.

R$_f$: 0.30 silica gel plate, developer: n-hexane/ethyl acetate (4/1))

(b) 3.4 g of L-N-benzyloxycarbonylcyclohexylalaninal was dissolved in 25 ml of dry tetrahydrofuran, and 36 ml of a 0.88M vinyl magnesium bromide tetrahydrofuran solution was dropwise added thereto at −78° C. under an argon stream over a period of 40 minutes. After the completion of the addition, the reaction mixture was raised to room temperature and stirred for 30 minutes at the same temperature. The reaction soltuion was poured into 250 ml of a saturated ammonium chloride aqueous solution and extracted with ethyl acetate. The ethyl acetate layer was washed with a saturated sodium chloride aqueous solution and dried over anhydrous magnesium sulfate. The solvent was distilled off under reduced pressure, and the residue was purified by silica gel column chromatography (Kiesel gel 60) by using tolluene/ethyl acetate (7/1) to obtain 1.9 g of the above-identified compound as a colorless oily substance.

R$_f$: 0.18 (silica gel plate, developer: n-hexane/ethyl acetate (4/1))

(3) 3-[(4S,5RS)-3-benzyloxycarbonyl-4-cyclohexylmethyl-2,2-dimethyloxazolidin-5-yl]-2-ethyl-2-propenoic acid isobutylamide (a) 983 mg of (3RS,4S)-4-benzyloxycarbonyl-amino-5-cyclohexyl-3-hydroxy-1-pentene was dissolved in 5 ml of dichloromethane, and 4 ml of 2,2-dimethoxypropane and 30 mg of anhydrous p-toluene sulfonic acid were added thereto. The mixture was stirred overnight at room temperature, and then 100 ml of ethyl acetate was added to the reaction mixure. The solution was washed sequentially with a saturated sodium hydrogen carbonate aqueous solution and a saturated sodium chloride aqueous solution, and dried over anhydrous magnesium sulfate. The solvent was distilled off under reduced pressure, and the residue was purified by silica gel column chromatography (Kiesel gel 60) by using n-hexane/ethyl acetate (20/1) to obtain 967 mg of (4S,5RS)-3-benzyloxycarbonyl-4-cyclohexylmethyl-5-ethenyl-2,2-dimethyloxazolidine as a colorless oily substance.

R$_f$: 0.74 (silica gel plate, developer: n-hexane/ethyl acetate (3/1))

(b) 960 mg of (4S,5RS)-3-benzyloxycarbonyl-4-cyclohexylmethyl-5-ethenyl-2,2-dimethyloxazolidine was dissolved in 7 ml of dioxane, and 5 ml of dioxane solution containing 35 mg of osmium tetraoxide was added thereto, and reacted for 15 minutes at room temperture in the absence of light. The reaction mixture was diluted with 2.5 ml of water, and 8 ml of a solution containing 1.15 g of sodium periodide was dropwise added over a period of 40 minutes. After the completion of the addition, the mixture was stirred for 1.5 hours at room temperature. Insolubles were filtered off, and the filtrate was diluted with 100 ml of diethyl ether. The diluted filtrate was washed sequentially with a 5% sodium sulfide solution, water and a saturated sodium chloride aqueous solution, and dried over anhydrous magnesium sulfate. The solvent was distilled off under reduced pressure to obtain 992 mg of (4S,5RS)-3-benzyloxycarbonyl-4-cyclohexylmethyl-5-formyl-2,2-dimethyloxazolidine as a colorless oily substance.

$R_f$: 0.40 (silica gel plate, developer: n-hexane/ethyl acetate (3/1))

(c) 176 mg of lithium chloride was suspended in 10 ml of dry tetrahydrofuran, and 834 mg of ethyl 2-diethylphosphonobutanoate was added thereto under an argon stream. The mixture was sitrred for 5 minutes at room temperature, and 630 mg of diazabicycloundecene was dropwise added thereto. The mixture was stirred for 10 minutes at room temperature and 10 ml of dry tetrahydrofuran solution of 990 mg of (4S,5RS)-3-benzyloxycarbonyl-4-cyclohexylmethyl-5-formyl-2,2-dimethyloxazolidine obtained in the above step (b) was added thereto and stirred overnight at room temperature. The reaction solution was adjusted to pH 3-4 with 0.5N hydrochloric acid and diluted with water. The solution was extracted with ethyl acetae and the organic layer was washed sequentially with water and a saturated sodium chloride aqueous solution, and dried over anhydrous sodium sulfate. The solvent was distilled off under reduced pressure, and the residue was purified by silica gel column chromatography (Kiesel gel 60) by using n-hexane/ethyl acetate (10/1) to obtain 965 mg of ethyl 3-[(4S,5RS)-3-benzyloxycarbonyl-4-cyclohexylmethyl-2,2-dimethyloxazolidin-5-yl]-2-ethyl-2-propenoate as a colorless oily substance.

$R_f$: 0.43 (silica gel plate, developer: n-hexane/ethyl acetate (5/1))

(d) 960 mg of the propenoate obtained in the above step (c) was dissolved in 5.3 ml of ethanol/water (10/1) solution of 2N potassium hydroxide, and stirred overnight at room temperature. The reaction solution was adjusted to pH 2 with 2N hydrochloric acid and extracted with ethyl acetate. The ethyl acetate layer was washed with a saturated sodium chloride aqueous solution and dried over anhydrous magnesium sulfate. The solvent was distilled off under reduced pessure to obtain 827 mg of the corresponding carboxylic acid as colorless oily substance. The carboxylic acid is dissolved in 7 ml of dimethylformamide, and 225 mg of triethylamine, 694 mg of diphenylphosphorylazide and 200 mg of isobutylamine were added thereto at −15° C. The mixture was stirred for 2 hours not higher than 0° C. and further stirred overnight at room temperature. 150 ml of ethyl acetate was added to the reaction solution, and the ethyl acetate layer was washed sequentially with 1N hydrochloric acid, water, a saturated sodium hydrogen carbonate, water, and a saturated sodium chloride aqueous solution and dried over anhydrous magnesium sulfate. The solvent was distilled off under reduced pressure, and the residue was purified by silica gel column chromatography (Kiesel gel 60) by using n-hexane/ethyl acetate (5/1) to obtain from the second fraction 120 mg of 3-[(4S,5S)-3-benzyloxycarbonyl-4-cyclohexylmethyl-2,2-dimethyloxazolidin-5-yl]-2-ethyl-2(Z)-propenoic acid isobutylamide as a colorless oily substance.

$R_f$: 0.36 (silica gel plate, developer: n-hexane/ethyl acetate (3/1))

NMR(300 MHz, CDCl$_3$) δppm: 2.15–2.32(1H, m), 2.32–2.50(1H, m), 3.10–3.30(2H, m), 3.75–3.95(1H, br), 4.50(2H, dd, J$_1$=2.4 Hz, J$_2$=8.7 Hz), 5.05–5.25(2H, m), 5.61(1H, d, J$_2$=8.7 Hz), 6.52–6.72(1H, br).

Further, 180 mg of a mixture of 3-[(4S,5S)-3-benzyloxycarbonyl-4-cyclohexylmethyl-2,2-dimethyloxazolidin-5-yl]-2-ethyl-2(E)-propenoic acid isobutylamide and 3-[(4S,5R)-3-benzyloxycarbonyl-4-cyclohexylmethyl-2,2-dimethyloxazolidin-5-yl]-2-ethyl-2(E)-propenoic acid isobutylamide was obtained from the fourth fraction as a colorless powder, and the mixture was further purified by silica gel column chromatography (Kiesel gel 60) by using n-hexane/ethyl acetate (5/1) to obtain 66 mg of 3-[(4S,5S)-3-benzyloxycarbonyl-4-cyclohexylmethyl-2,2-dimethyloxazolidin-5-yl]-2-ethyl-2(E)-propenoic acid isobutylamide as a colorless oily substance.

$R_f$: 0.29 (silica gel plate, developer: n-hexane/ethyl acetate (3/1))

NMR(300 MHz, CDCl$_3$): δppm: 2.20–2.52(2H, m), 3.05–3.20(2H, m), 3.80–3.95(1H, br), 4.60(1H, dd, J$_1$=3.0 Hz, J$_2$=9.0 Hz), 5.02–5.20(2H, m), 5.70–5.82(1H, br), 6.80(1H, d, J$_2$=9.0 Hz).

(4) (2E,4S,5S)-5-(L-N-benzyloxycarbonylnaphthylalanyl-L-norleucyl)amino-6-cyclohexyl-2-ethyl-4-hydroxy-2-hexenoic acid isobutylamide 56 mg of 3-[(4S,5S)-3-benzyloxycarbonyl-4-cyclohexylmethyl-2,2-dimethyloxazolidin-5-yl]-2-ethyl-2(E)-propenoic acid isobutylamide was dissolved in 1.5 ml of ethanol, and hydrogenated by using 5 mg of 10% palladium carbon as catalyst for 2.5 hours at room temperature under atmospheric pressure. The catalyst was filtered off and the residue was distilled off under reduced pressure. The residue was dissolved in 1 ml of dimethylformamide, and 54 mg of L-N-benzyloxycarbonylnaphthylalanyl-L-norleucine, 39 mg of diphenylphosphorylazide and 14 mg of triethylamine were added thereto at −15° C. The mixture was stirred for 2 hours at a temperature from −15° to 0° C., and further stirred overnight at room temperature. Water was added to the reaction mixture and the crystal precipitated was collected by filtration and dried under reduced pressure. The crystal was purified by silica gel column chromatography (Kiesel gel 60) by using n-hexane/ethyl acetate (7/4) to obtain 27 mg of the above-identified compound as a colorless powder.

Melting point: 82°–86° C.

$R_f$: 0.54 (silica gel plate, developer: chloroform/methanol (40/1))

NMR(300 MHz, CDCl$_3$): δppm: 0.70–1.95(30H, m), 2.30–2.55(2H, m), 3.07–3.20(2H, m), 3.45–3.60(3H, m), 4.35–4.55(1H, m), 4.62(1H, d, J=8.8 Hz), 4.84(1H, t, J=7.4 Hz), 5.04(2H, s), 5.30(1H, dd, J=8.2 Hz, 2.3 Hz), 5.30–5.47(1H, br), 5.75–5.87(1H, br), 6.10(1H, d, J=8.8 Hz), 6.51(1H, d, J=6.8 Hz), 7.20–7.45(7H, m), 7.45–7.65(2H, m), 7.78(1H, d, J=7.8 Hz), 7.86(1H, d, J=7.8 Hz), 8.20(1H, brs).

EXAMPLE 10

(4S,5S)-5-(L-N-benzyloxycarbonylnaphthylalanyl-L-norleucyl)amino-4-hydroxy-2-ethyl-7-methyl-2(E)-octenoic acid 4picolylamide 58 mg of 3-[(4S,5S)-3-benzyloxycarbonyl-2,2-dimethyl-4-isobutyloxazolidin-5-yl]-2-ethyl-2(E)-propenoic acid 4-picolylamide was obtained by using 3-[(4S,5S)-3-benzyloxycarbonyl-2,2-dimethyl-4-isobutyloxazolidin-5-yl]-2-ethyl-2-propenoic acid and 4-picolylamine in accordance with Example 2-2)-(b), and deprotected in accordance with Example 2-3). Then, the deprotected product was subjected to coupling with 40 mg of L-N-benzyloxycarbonylnaphthylalanyl-L-norleucine to obtain 4.9 mg of the above-identified compound as a colorless powder.

$R_f$: 0.13 (silica gel plate, developer: chloroform/methanol (20/1))

NMR(300 MHz, CDCl$_3$): δppm: 0.70–0.96(9H, m), 0.96–1.92(12H, m), 2.37–2.57(2H, m), 3.36–4.75(8H, m), 4.93(1H, d, J=13 Hz), 5.05(1H, d, J=13 Hz), 6.11(1H, d, J=8.6 Hz), 7.17–7.42(9H, m), 7.42–7.65(2H, m), 7.65–7.92(2H, m), 8.13(1H, br s), 8.38(1H, br s), 8.48–8.61(1H, m).

EXAMPLE 11

(4S,5S)-5-(L-N-benzyloxycarbonylnaphthylalanyl-L-norleucyl)amino-4-hydroxy-2-ethyl-7-methyl-2(E)-octenoic acid morpholinoethylamide 30 mg of 3-[(4S,5S)-3-tert-butoxycarbonyl-2,2-dimethyl-4-isobutyloxazolidin-5-yl]-2-ethyl-2(E)-propenoic acid morpholinoethylamide was obtained by using 3-[(4S,5S)-3-tert-butoxycarbonyl-2,2-dimethyl-4-isobutyloxazolidin-5-yl]-2-ethyl-2-propenoic acid and N-(2-aminoethyl)morpholine in accordance with Example 2-2)-(b), and deprotected by using 0.3 ml of a 10% hydrochloric acid/methanol. Then, the deprotected product was subjected to coupling with 21 mg of L-N-benzyloxycarbonylnaphthylalanyl-L-norleucine to obtain 15 mg of the above-identified compound as a white powder.

$R_f$: 0.17 (silica gel plate developer: chloroform/methanol (20/1))

NMR(300 MHz, CDCl$_3$): δppm: 0.85(3H, t, J=7.7 Hz), 0.92(6H, d, J=7.7 Hz), 1.04(3H, t, J=7.7 Hz), 1.17–1.31(2H, m), 1.35–1.80(7H, m), 2.27–2.52(6H, m), 2.56(2H, t, J=7.7 Hz), 3.36–3.52(6H, m), 3.55–3.72(5H, m), 3.88–4.01(1H, m), 4.06–4.16(1H, m), 4.38(1H, dd, J=4.3, 8.6 Hz), 4.48(1H, dd, J=6.9, 8.6 Hz), 5.00(1H, d, J=13 Hz), 5.11(1H, d, J=13 Hz), 5.99(1H, d, J=8.6 Hz), 7.18–7.45(7H, m), 7.45–7.65(2H, m), 7.81(1H, d, J=8.6 Hz), 7.90(1H, d, J=8.6 Hz), 8.08(1H, d, J=8.6 Hz).

EXAMPLE 12

(4S,5S)-5-(L-N-benzyloxycarbonylnaphthylalanyl-L-norleucyl)amino-4-hydroxy-2,7-dimethyl-2(E)-octenoic acid isobutylamide 249 mg of ethyl 3-[(4S,5S)-3-tert-butoxycarbonyl-2,2-dimethyl-4-isobutyloxazolidin-5-yl]-2-methyl-2-propenoate was obtained by using 174 mg of ethyl 2-diethylphosphonopropenoate and 174 mg of (4S,5R)-3-tert-butoxycarbonyl-2,2-dimethyl-5-formyl-4-isobutyloxazolidine in accordance with Example 2. 225 mg of the compound thus obtained was subjected to alkali saponification, and then condensed with isobutylamine to obtain 22.5 mg of Z-isomer, 45.9 mg of E-isomer and 89.7 mg of a EZ-mixture of 3-[(4S,5S)-3-tert-butoxycarbonyl-2,2-dimethyl-4-isobutyloxazolidin-5-yl]-2-methyl-2-propenoic acid isobutylamide, respectively. 0.4 ml of a 10% hydrochloric acid/methanol solution was added to 33.5 mg of the E-isomer at room temperature to remove the protecting group, followed by condensation with L-N-benzyloxycarbonylnaphthylalanyl-L-norleucine using diphenylphosphorylazide to obtain 31.3 mg of the above-identified compound.

$R_f$: 0.42 (silica gel plate, developer: chloroform/methanol (20/1))

Mass spectrum 701 (M$^+$+1)

NMR(300 MHz, CD$_3$OD): δppm: 0.8–1.85(25H), 1.9(3H, s), 2.95(2H, d, J=7 Hz), 3.68(1H, dd), 4.02(1H, m), 4.22(1H, m), 4.4(1H, m), 4.55(2H, m), 6.07(1H, d, J=7 Hz), 7.2–7.4(8H, m), 7.75(2H, m), 7.87(1H, d), 8.16(1H, d).

The compound of the present invention has strong activities to inhibit renin which is involved in a renin-angiotensin hypertensive system and thus expected to be useful as curing agent of hypertension due to the progress of the renin-angiotensim system.

We claim:

1. A compound or its salt represented by the formula:

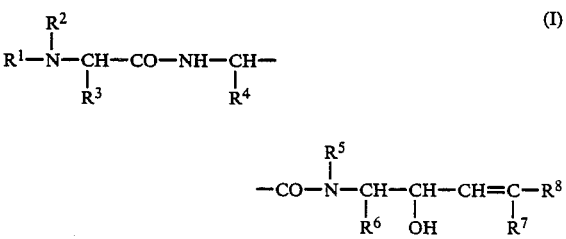

wherein each of R$^1$ and R$^2$ which may be the same or different is a hydrogen atom, a lower alkyl group, an aralkyl group, a lower alkoxycarbonyl group, an aryloxycarbonyl group, an aralkyloxycarbonyl group or a lower alkanoyl group which may be substituted by from one to three substituents selected from the group consisting of an amino group, a hydroxyl group, a carboxyl group, an aryloxy group, an aralkyloxycarbonylamino group, a lower alkoxycarbonylamino group and a

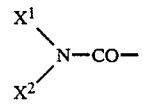

group (wherein each of X$^1$ and X$^2$ which may be the same or different is a hydrogen atom, a lower alkyl group, an aryl group or an aralkyl group, or X$^1$ and X$^2$ form together with the adjacent nitrogen atom a 5- or 6-membered heterocyclic group which may further contain a hetero atom selected from the group consisting of a nitrogen atom, an oxygen atom and a sulfur atom) and which may further contain a double bond in its carbon chain, each of R$^3$, R$^4$ and R$^6$ which may be the same or different is a hydrogen atom, a lower alkyl group, a cycloalkyl group, a cycloalkylalkyl group, an aryl group, an aralkyl group or a residue of an acidic, neutral or basic amino acid, R$^5$ is a hydrogen atom or a lower alkyl group, R$^7$ is a hydrogen atom, a lower alkyl, cycloalkyl, cycloalkylalkyl or aralkyl group which may be substituted by one or two hydroxyl groups or a residue of an acidic, neutral or basic amino acid, and R$^8$ is a hydroxymethyl group or a —CO—R$^9$ group (wherein R$^9$ is a hydroxyl group, a —OY group (wherein Y is a lower alkyl group, an aryl group, an aralkyl group, a lower alkoxyalkyl group, a lower alkanoyloxyalkyl group, a lower akloxycarbonyloxyalkyl group, or a 1-phthalidyl group) or a

group (wherein each of $Y^1$ and $Y^2$ which may be the same or different is a hydrogen atom, a lower alkyl group, an aryl group, an aralkyl group or a cycloalkyl group, or $Y^1$ and $Y^2$ form together with the adjacent nitrogen atom a 5- or 6-membered heterocyclic group which may further contain a hetero atom selected from the group consisting of a nitrogen atom, an oxygen atom and a sulfur atom)).

2. The compound according to claim 1, which is (4S,5S)-5-(L-N-benzyloxycarbonylnaphthylalanyl-L-norleucyl)amino-4-hydroxy-7-methyl-2(E)-octenoic acid isobutylamide.

3. The compound according to claim 1, which is (4S,5S)-5-(L-N-benzyloxycarbonylnaphthyl-alanyl-L-norleucyl)amino-2-ethyl-4-hydroxy-7-methyl-2(E)-octenoic acid isobutylamide.

4. The compound according to claim 1, which is (4S,5S)-5-(L-N-benzyloxycarbonylnaphthylalanyl-L-norleucyl)amino-2-ethyl-4-hydroxy-7-methyl-2(Z)-octenoic acid isobutylamide.

5. The compound according to claim 1 which is (4S,5S)-5-(L-N-benzyloxycarbonylnaphthylalanyl-L-norleucyl)amino-4-hydroxy-2-propyl-7-methyl-2(E)-octenoic acid isobutylamide.

6. The compound according to claim 1 which is (4S,5S)-5-(L-N-benzyloxycarbonylnaphthylalanyl-L-norleucyl)amino-4-hydroxy-2-propyl-7-methyl-2(Z)-octenoic acid isobutylamide.

7. The compound according to claim 1 which is (4S,5S)-5-(L-N-benzyloxycarbonylnaphthylalanyl-L-norleucyl)-amino-4-hydroxy-2-isopropyl-7-methyl-2(E)-octenoic acid isobutylamide.

8. The compound according to claim 1 which is (4S,5S)-5(L-N-benzyloxycarbonyl-naphthylalanyl-L-norleucyl)amino-4-hydroxy-2-isopropyl-7-methyl-2(Z)-octenoic acid isobutylaimide.

9. The compound according to claim 1 which is (4S,5S)-5-(L-N-benzyloxycarbonylnaphylalanyl-L-norleucyl)-amino-4-hydroxy-2-(3-hydroxypropyl)-7-methyl-2(E)-octenoic acid isobutylamide.

10. A hypotensive drug comprising an effective amount of the compound of the formula I as defined in claim 1 and a pharmaceutically acceptable carrier.

11. A process for producing a compound or its salt represented by the formula:

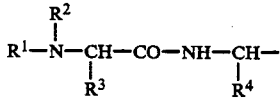
(I)

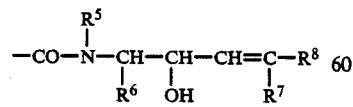

wherein each of $R^1$ and $R^2$ which may be the same or different is a hydrogen atom, a lower alkyl group, an aralkyl group, a lower alkoxycarbonyl group, an aryloxycarbonyl group, an aralkyloxycarbonyl group or a lower alkanoyl group which may be substituted by from one to three substituents selected from the group consisting of an amino group, a hydroxyl group, a carboxyl group, an aryloxy group, an aralkyloxycarbonylamino group, a lower alkoxycarbonylamino group and a

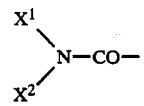

group (wherein each of $X^1$ and $X^2$ which may be the same or different is a hydrogen atom, a lower alkyl group, an aryl group or an aralkyl group, or $X^1$ and $X^2$ form together with the adjacent nitrogen atom a 5- or 6-membered heterocyclic group which may further contain a hetero atom selected from the group consisting of a nitrogen atom, an oxygen atom and a sulfur atom) and which may further contain a double bond in its carbon chain, each of $R^3$, $R^4$ and $R^6$ which may be the same or different is a hydrogen atom, a lower alkyl group, a cycloalkyl group, a cycloalkylalkyl group, an aryl group, an aralkyl group or a residue of an acidic, neutral or basic amino acid, $R^5$ is a hydrogen atom or a lower alkyl group, $R^7$ is a hydrogen atom, a lower alkyl, cycloalkyl, cycloalkylalkyl or aralkyl group which may be substituted by one or two hydroxyl groups or a residue of an acidic, neutral or basic amino acid, and $R^8$ is a hydroxymethyl group or a —CO—$R^9$ group (wherein $R^9$ is a hydroxyl group, a —OY group (wherein Y is a lower alkyl group, an aryl group, an aralkyl group, a lower alkoxyalkyl group, a lower alkanoyloxyalkyl group, a lower akloxycarbonyloxyalkyl group, or a 1-phthalidyl group) or a

group (wherein each of $Y^1$ and $Y^2$ which may be the same or different is a hydrogen atom, a lower alkyl group, an aryl group, an aralkyl group or a cycloalkyl group, or $Y^1$ and $Y^2$ form together with the adjacent nitrogen atom a 5- or 6-membered heterocyclic group which may further contain a hetero atom selected from the group consisting of a nitrogen atom, an oxygen atom and a sulfur atom)), which comprises reacting a compound of the formula:

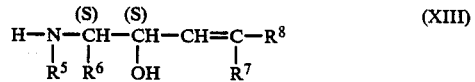
(XIII)

wherein $R^5$, $R^6$, $R^7$ and $R^8$ are as defined above, with a compound of the formula:

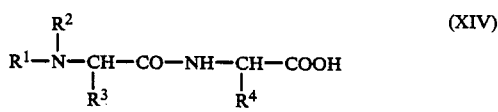
(XIV)

wherein $R^1$, $R^2$, $R^3$ and $R^4$ are as defined above.

* * * * *